United States Patent
Hristov et al.

(10) Patent No.: US 9,949,823 B2
(45) Date of Patent: Apr. 24, 2018

(54) UNIVERSAL BIOABSORBABLE NASAL IMPLANT KIT

(71) Applicant: Ethicon, Inc., Somerville, NJ (US)

(72) Inventors: Krasimira Hristov, Belle Mead, NJ (US); Gaoyuan Gavin Chen, Hillsborough, NJ (US); Mark T. Mooney, Johns Creek, GA (US); James A. Matrunich, Mountainside, NJ (US); Jianxin Guo, Livingston, NJ (US); Emil Richard Skula, Wayne, NJ (US)

(73) Assignee: Ethicon, Inc, Somerville, NJ (US)

( * ) Notice: Subject to any disclaimer, the term of this patent is extended or adjusted under 35 U.S.C. 154(b) by 64 days.

(21) Appl. No.: 14/704,006

(22) Filed: May 5, 2015

(65) Prior Publication Data
US 2015/0230917 A1    Aug. 20, 2015

Related U.S. Application Data

(62) Division of application No. 13/477,474, filed on May 22, 2012, now abandoned.

(51) Int. Cl.
*A61F 2/18* (2006.01)

(52) U.S. Cl.
CPC ...... *A61F 2/186* (2013.01); *A61F 2210/0004* (2013.01)

(58) Field of Classification Search
CPC .... A61F 2/186; A61F 5/08; A61F 2/18; A61F 2/0059; A61F 2210/0004
See application file for complete search history.

(56) References Cited

U.S. PATENT DOCUMENTS

| | | | |
|---|---|---|---|
| 1,105,105 | A | 7/1914 | Sherman |
| 3,978,185 | A | 8/1976 | Buntin et al. |
| D261,935 | S | 11/1981 | Halloran |
| 4,378,802 | A | 4/1983 | Ersek |
| 4,429,690 | A | 2/1984 | Angelino Pievani |
| 4,457,756 | A | 7/1984 | Kern et al. |
| 4,863,974 | A | 9/1989 | Mallouk |
| 4,905,680 | A | 3/1990 | Tunc |
| 4,994,084 | A | 2/1991 | Brennan |

(Continued)

FOREIGN PATENT DOCUMENTS

| | | |
|---|---|---|
| CN | 2439847 | 7/2001 |
| DE | 20307058 | 9/2003 |

(Continued)

OTHER PUBLICATIONS

Ansari, K. MD, FRCSC, "Grafts and implants in rhinoplasty—Techniques and longterm results", Operative Techniques in Otolaryngology (2008) 19, pp. 42-58.

(Continued)

*Primary Examiner* — Dianne Dornbusch
*Assistant Examiner* — Michael Mendoza

(57) ABSTRACT

Novel bioabsorbable, universal kits used to form nasal implants are disclosed. The implants are useful in rhinoplasty and nasal reconstruction surgical procedures. The kit devices have a universal configuration and can be converted by the surgeon in the field into one or more individual nasal implant devices having different configurations and applications. The kits may have outlines of nasal implants thereon.

15 Claims, 24 Drawing Sheets

(56) References Cited

U.S. PATENT DOCUMENTS

| | | | |
|---|---|---|---|
| 5,002,583 | A | 3/1991 | Pitaru |
| 5,069,660 | A | 12/1991 | Grantham |
| 5,112,353 | A | 5/1992 | Johansson |
| 5,275,601 | A | 1/1994 | Gogolewski |
| 5,413,600 | A | 5/1995 | Mittleman |
| D366,526 | S | 1/1996 | Rizzo |
| 5,496,371 | A | 3/1996 | Eppley |
| 5,620,452 | A | 4/1997 | Yoon |
| 5,674,286 | A | 10/1997 | D'Alessio |
| 5,863,297 | A | 1/1999 | Walter |
| 5,868,746 | A | 2/1999 | Sarver |
| 6,106,541 | A | 8/2000 | Hurbis |
| 6,228,111 | B1 | 5/2001 | Tormala et al. |
| 6,322,590 | B1 | 11/2001 | Sillers |
| 6,454,803 | B1 | 9/2002 | Romo, III |
| 6,516,806 | B2 | 2/2003 | Knudson |
| 6,971,252 | B2 * | 12/2005 | Therin .................. A61F 2/0045 66/170 |
| 7,740,630 | B2 | 6/2010 | Michelson |
| 2005/0015088 | A1 | 1/2005 | Ringeisen |
| 2005/0085817 | A1 | 4/2005 | Ringeisen |
| 2005/0288790 | A1 | 12/2005 | Swords |
| 2006/0224242 | A1 | 10/2006 | Swords |
| 2007/0061015 | A1 | 3/2007 | Jensen |
| 2007/0213828 | A1 | 9/2007 | Trieu |
| 2007/0270899 | A1 | 11/2007 | aWengen |
| 2007/0293946 | A1 | 12/2007 | Gonzales et al. |
| 2008/0058858 | A1 | 3/2008 | Smith |
| 2008/0077240 | A1 | 3/2008 | Saidi |
| 2008/0196729 | A1 | 8/2008 | Browning |
| 2008/0234818 | A1 | 9/2008 | Kang |
| 2009/0062846 | A1 | 3/2009 | Ken |
| 2009/0069904 | A1 | 3/2009 | Picha |
| 2009/0157194 | A1 | 6/2009 | Shikinami |
| 2009/0170927 | A1 | 7/2009 | Bezwada |
| 2009/0177272 | A1 | 7/2009 | Abbate et al. |
| 2009/0270308 | A1 | 10/2009 | Libin et al. |
| 2009/0292358 | A1 | 11/2009 | Saidi |
| 2010/0076555 | A1 | 3/2010 | Marten |
| 2010/0185282 | A1 | 7/2010 | Jung |
| 2012/0078367 | A1 | 3/2012 | Hristov et al. |
| 2012/0165957 | A1 * | 6/2012 | Everland ............... A61F 2/0045 623/23.72 |
| 2012/0215307 | A1 | 8/2012 | Chen et al. |

FOREIGN PATENT DOCUMENTS

| | | |
|---|---|---|
| DE | 202004021075 | 9/2006 |
| DE | 102006023058 | 10/2007 |
| EP | 1475056 A1 | 11/2004 |
| EP | 1475056 B1 | 10/2010 |
| WO | WO 2008/153263 | 12/2008 |

OTHER PUBLICATIONS

Boenisch M., M.D., "Healing process of cartilage in connection with PDS Foil" HNO (2000) 48:743 5 pages.

Boenisch M., MD., "Influence of Polydioxanone Foil on Growing Septal Cartilage after Surgery in an Animal Model", Archives of Facial Plastic Surgery, Jul./Aug. 2003.,vol. 5 pp. 316-319.

Echeverry, A. MD et al "Alternative Technique for Tip Support in Secondary Rhinoplasty" Aesthetic Surgery Journal —Nov./Dec. 2006 26(6) pp. 662-668.

Gubisch, W. MD, "Extracorporeal Septoplasty for the Markedly Deviated Septum", Archives of Facial Plastic Surgery, Jul./Aug. 2005, vol. 7 pp. 218-226.

James, S.E. (Plast.) et al "Cartilage Recycling in Rhinoplasty: Polydioxanone Foil as an Absorbable Biomechanical Scaffold", Plastic and Reconstructive Surgery Jul. 2008, vol. 122, No. 1, pp. 254-260.

Kim, Y.O. et al, "Aesthetic reconstruction of the nasal tip using a folded composite graft from the ear", The British Association of Plastic Surgeons (2004) 57, pp. 238-244.

Eppley, B. "LactoSorb Grafting for Cartilage Preservation in Rhinoplasty" http://exploreplasticsurgery.com/2008/06/29/lactosorb-grafting-for-cartilage-A42preservation-in-rhinoplasty/ (2008), 2 pages.

"LactoSorb® : The Proven Leader in Resorbable Technology" (http://www.lorenzsurgical.com/category.php?cat=5 (2011) , 1 page.

Lawson, W. et al,"The Silicone Columellar Strut", Plastic and Reconstructive Surgery, Apr. 1996 vol. 97(5) Supplement pp. 938-943.

Lovice, D.B. et al, "Grafts and Implants in Rhinoplasty and Nasal Reconstruction" Otolaryngologic Clinics of North America (1999) 32(1) pp. 113-141.

Romo, T. III, et al"Nasal Grafts and Implants in Revision Rhinoplasty" Facial Plast Surg Clin N Am (2006) 14 pp. 373-387.

Romo, T. III, et al,"Nasal Implants", Facial Plast Surg Clin N Am (2008) 16 pp. 123-132.

Stal, S. M.D. et al, "The Use of Resorbable Spacers for Nasal Spreader Grafts", Plastic and Reconstructive Surgery, Sep. 2000, vol. 106, No. 4 , pp. 922-928.

Toriumi, D. "New Concepts in Nasal Tip Contouring", Archives of Facial Plastic Surgery, vol. 8 May/Jun. 2006, pp. 156-185.

Watzinger, F. et al., "Biodegradable polymer membrane used as septal splint" Int. J. Oral Maxillofac. Surg. 2008; 37: pp. 473-477.

http://www.hansonmedical.com/nasal.html (2010) 2 pages.

http://www.porexsurgical.com/english/surgical/snasaldartt.asp MEDPOR® Nasal DARTT Implant (2010) 1 page.

International Preliminary Report on Patentability re: PCT/US2011/053242 dated Apr. 2, 2013.

International Search Report re: PCT/US2011/053242 dated Dec. 6, 2011.

International Preliminary Report on Patentability re: PCT/US2012/025614 dated Aug. 21, 2013.

International Search Report re: PCT/US2012/025614 dated Jun. 4, 2012.

International Search Report re: PCT/US2013/042144 dated Aug. 5, 2013.

Written Opinion re: PCT/US2013/042144 dated Aug. 5, 2013.

* cited by examiner

UNIVERSAL BIOABSORBABLE NASAL IMPLANT KIT

This application is a divisional of U.S. application Ser. No. 13/477,474, filed May 22, 2012. The complete disclosure of the aforementioned U.S. patent application is hereby incorporated herein by reference for all purposes.

FIELD OF THE INVENTION

The field of art to which this invention relates is bioabsorbable implantable medical devices, in particular, bioabsorbable implantable medical devices for use in nasal aesthetic and reconstructive surgical procedures.

BACKGROUND OF THE INVENTION

The human nose is a relatively complex structure that allows for the inhalation of air and exhalation of air and carbon dioxide and other cellular waste products. The nose also accomplishes physiological functions including humidification, temperature control and filtration of the inspired air. The nose additionally is a sensory organ responsible for the olfactory sense. For most people, the nose performs these functions efficiently and relatively trouble-free. However, patients often complain of symptoms relating to restricted airflow in their nasal passages. The septal cartilage structure of the nose divides the nose into two passages. These passages are typically described or referred to as nostrils. Inspired air moves through the nostrils, the nasal vault, and the nasopharyngeal wall, the pharynx, larynx, trachea, bronchi and reaches the alveoli in the lungs. Inhalation and exhalation are responsive to movement of the diaphragm and the intercostal muscles of the ribs. It is estimated that more than fifty percent of the total respiratory resistance of the respiratory tract occurs in the nose. It is known that airway obstruction in the nose may be attributable to various factors, including deviated septum, suboptimal position and rigidity of the lateral nasal walls, etc. The internal nasal valve is described as the space between the fold of the upper lateral cartilage (ULC) and the nasal septum. The angle between the septum and the upper lateral cartilage normally ranges between 10 and 15 degrees. It is generally accepted that nasal resistance behaves in accordance with Poiseuille's law and Bernoulli's principle, which means that small changes in the nasal valve area tend to have an exponential effect on the airflow. Patients with less than a ten degree angle at the internal nasal valve usually have airflow obstruction and are diagnosed with internal valve stenosis. The internal nasal valve may also be narrowed due to thickening of the septum or by a deviated septum. Additional causes of nasal obstruction include trauma to the nose, face or head, burns, and elective surgery. Surgery of the nose typically involves repositioning of the nose's bony and cartilaginous structures. Excessive scarring disc to aggressive resection may also lead to resultant narrowing of the nasal valve area. The internal valve may also become collapsed due to poor cartilage quality or position. As the internal valve collapses, the airflow becomes obstructed. The external nasal valve is composed of the nasal ala and supporting structures of the lower lateral cartilages.

These areas are named valves because they regulate the cross-sectional area of the nasal airway and perform dynamic functions. The collapse of the lateral nasal walls at the internal valve is known to be associated with a reduction rhinoplasty procedure commonly referred to as 'hump removal'. During such reduction rhinoplasty, a hump in the cartilaginous and/or bony dorsum of the nose needs to be resected, which leads to reduction of the overall valve area and destabilizing of the ULC. The patient may experience post-surgical breathing problems if the nasal valve is not properly repaired after this procedure. This nasal valve reconstruction is typically done by the surgeon emplacing unilateral or bi-lateral spreader grafts on the nasal septum from the cephalic to the caudal portion of the nasal septum. Such devices and procedures widen the cross-sectional area of the upper nasal valve. However, there are deficiencies present in and associated with the use of conventional spreader grafts, which are typically made from autologous cartilage. The deficiencies include the need for autologous cartilage harvesting, resulting in donor site morbidity, and increased pain and duration of the procedure. Although non-absorbable spreader graft implants exist, surgeons prefer not to use them due to the increase risk of complications such as infection and extrusion.

Therefore, there is a need in this art for novel bioabsorbable, spreader grafts for nasal reconstruction procedures that increase the spacing between nasal upper lateral cartilages without using permanent foreign body material to achieve permanent repositioning of the upper lateral cartilages, and, which provide improved structural support in patients undergoing plastic or reconstructive surgical nasal procedures. There is also a need for novel bioabsorbable spreader grafts which promote tissue ingrowth and minimize long term complications, are relatively easy for the surgeon to implant, and provide a superior result and outcome for the patient.

As mentioned previously, rhinoplasty is a complex surgical procedure that involves the modification of underlying nasal structures such as bone, cartilage, ligaments and soft fibro-fatty tissue. The procedure may be performed for a variety of reasons that include improving the aesthetic appearance of the patient's nose; for reconstructive purposes following trauma; correcting various abnormalities of the nose that the patient may present; and, for correcting nasal passage functional problems associated with breathing for both inhalation and expiration. Regardless of the reasons for the rhinoplasty, the surgeon strives to restore or maintain functionality, remediate structural issues, and at the same time address aesthetic factors by creating and/or maintaining certain proportions between the various parts of the nose and face.

One of the most challenging aspects of rhinoplasty is generally considered to be the surgery of the lower third of the nose, mainly the nasal lip region. The stability of the nasal tip is important not only for the aesthetic look and appearance of the nose (e.g., tip projection and tip rotation), but also for physiological and anatomical functions such as appropriate inspiration and expiration, facial expression, and shock absorbance in response to facial trauma.

Preserving or creating adequate support of the nasal tip is important for both the immediate post-operative results, and, the long-term outcomes over the life of the patient. Due to factors such as scar contracture, thinning of the soft tissue envelope, and weakening of the cartilage structures with aging, some suboptimal results may be observed soon after surgery, and not infrequently. The consequent deficiencies can often become much more obvious, pronounced, apparent, and prevalent with the passage of time, usually about ten to fifteen years later.

It is known that skin thickness is a factor in determining how well the external skin cover will redrape over the underlying structures of the nose post-surgery. Patients with thin skin tend to have stronger cartilaginous structures, but the underlying structures are more visible, and a step-like transition between the bone and the cartilage can be seen. On the other hand, for patients having thick skin, obtaining proper definition and refinement can be a challenge.

One of the major support mechanisms of the nasal tip is the medial crura of the lower lateral cartilage (LLC). The foundation of the nasal tip is determined by the base (anterior nasal spine) and the footplates of the medial crura. Patients who have long and strong medial crura that extend to the nasal spine are more likely to have adequate tip support. In contrast, patients who have short medial crura, and flaring footplates at the mid-columella, are more likely to have poor tip support and lose tip projection after surgery.

Various surgical techniques and procedures that provide long-term support to the tip of the nose and stabilization of the nasal base have been used in the past. One of the widely used techniques is the placement of a columellar strut graft. The graft is usually and typically made of autologous septal or rib cartilage, which is sutured between the medial crus of the lower lateral cartilages. The columellar strut graft can extend to the nasal spine or be placed above the nasal spine. Another surgical method or procedure to provide nasal tip projection and support is the "tongue-in-the-groove" technique, wherein the medial crus of the lower lateral cartilages are sutured to the caudal end of the septum. A septal extension graft may also be used to ensure that the nasal tip projection is maintained postoperatively, or to correct an over-rotated tip in the case of revision surgery. Although nonabsorbable implants may be used to support the nasal tip, such a method of tip support treatment is not preferred by surgeons because of associated complications, including infection, skin necrosis, and implant extrusion, as well as factors such as patient awareness, and appearance.

In order to improve existing surgical procedures and patient outcomes, there is a continuing need in this art for low mass columellar struts with geometric characteristics that enhance the associated implantation procedure and provide for superior patient results. In particular, there is a need in this art for novel implants made from bioabsorbable polymers that are useful in nasal reconstruction surgical procedures.

A septal extension graft is typically constructed from a piece of autologous cartilage, which is connected to the septum to increase the nasal length and ensure appropriate nasal labial angle. The cartilage graft is connected to the native septum in a "end to end" fashion by means of additionally harvested strips of cartilage that are fixated on one or both sides of the septum and stabilize the structures. This current method requires additional harvested cartilage to achieve the repair and the cartilage strips add additional thickness and thus reduce the airflow though the nasal passages. There is a similar need for novel bioabsorbable polymeric septal extension grab devices.

Bioabsorbable polymeric plates are also known in the art for use in nasal reconstructive procedures. For example, the PDS Flexible Plate distributed by Ethicon, Inc., Somerville, N.J., may be used by the surgeon for nasal soft tissue and cartilage reconstruction to aid septoplasty and the construction of various grafts in rhinoplasty.

Since many nasal reconstructive procedures are directed to correcting multiple nasal structural deficiencies, it is often common to use a multiplicity of grafts and/or devices in one procedure, including but not limited to columellar struts and spreader grafts, as well as plates, septal extensions, etc. Accordingly, the hospital or health care provider is required to maintain an inventory of such devices in multiple sizes. It would be advantages to have a single polymeric bioabsorbable universal kit device that could be cut or trimmed by the surgeon in the field to form a variety of sizes and types of bioabsorbable nasal implant devices. It would be also desirable to have single unitary kit device that could be cut into several different devices.

SUMMARY OF THE INVENTION

Accordingly a novel universal kit for use in nasal reconstructive procedures is disclosed. The kit is made from biocompatible polymers, in particular bioabsorbable polymers. The biocompatible, bioabsorbable polymeric nasal kit device has a first wall member having an inner surface, an outer surface a free top side, a bottom side, opposed lateral sides, and a first height. The kit device also has a second wall member having an inner surface, an outer surface, a free top side, a bottom side, opposed lateral sides and a second height, wherein the first height is greater than the second height. The device has a spine member having an inner surface and an outer surface. The bottom sides of the first and second wall members are connected to the spine member such that there is a channel defined by the inner surfaces of the first wall member, the second wall member, and the spine member. The kit device has an outline of at least one nasal implant on at least one of the members.

Another aspect of the present invention is a novel universal kit for use in nasal reconstructive procedures. The kit is made from biocompatible polymers, in particular bioabsorbable polymers. The biocompatible, bioabsorbable polymeric nasal kit device has a first wall member having an inner surface, an outer surface, a free top side, a bottom side, opposed lateral sides, and a first height. The kit device also has a second wall member having an inner surface, an outer surface, a free top side, a bottom side, opposed lateral sides and a second height, wherein the first height is greater than the second height. The device has a spine member having an inner surface and an outer surface. The bottom sides of the first and second wall members are connected to the spine member such that there is a channel defined by the inner surfaces of the first wall member, the second wall member, and the spine member.

Another aspect of the present invention is a method of forming a nasal implant device from the novel kits of the present invention.

Yet another aspect of the present invention is a method of using the above-mentioned kits in various nasal reconstructive surgical procedures.

These and other aspects and advantages of the present invention will be more apparent from the following description and accompanying drawings.

BRIEF DESCRIPTION OF THE DRAWINGS

FIG. 13B shows additional kit material optionally cut away to reduce the mass of the implant.

DETAILED DESCRIPTION OF THE INVENTION

Figure 1:
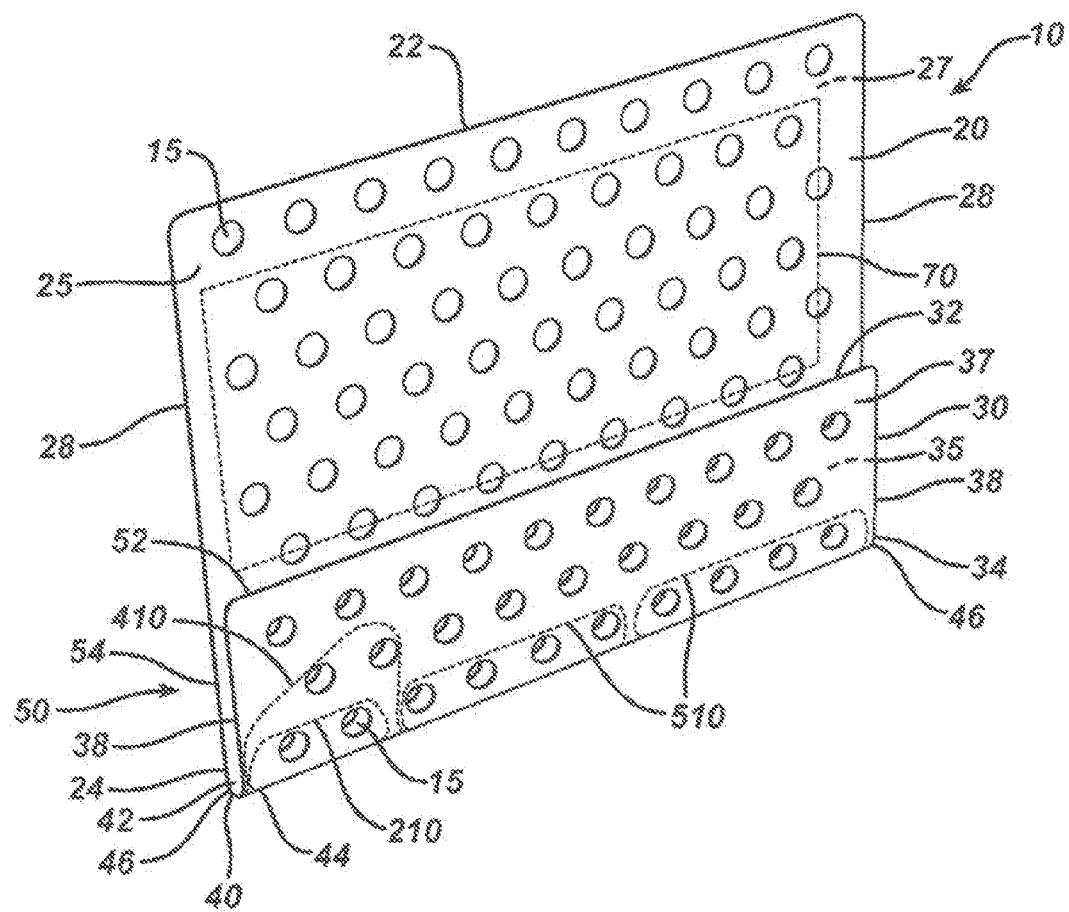
FIG. 1 is a perspective view of a universal kit device of the present invention; the device has perforations and outlines of several nasal implant devices.

The novel nasal kit devices of the present invention are made from conventional biocompatible and bioabsorbable materials. The bioabsorbable polymers useful to manufacture the devices of the present invention have several desirable properties, including good initial strength and breaking strength retention (BSR) and good bioabsorption, for example having sufficient BSR after implantation for a period of 6-20 weeks, and essentially complete bioabsorption in about 6-12 months. However, other strength and absorption profiles may be designed for a particular application.

A tensile test is one of the well known mechanical tests commonly used to evaluate a material's mechanical property (strength, modulus, elongation, etc.). The test determines the tensile breaking strength (or peak tensile force) and the tensile load at a givers elongation when a sample is elongated to break or to a pre-determined elongation. An Instron mechanical tester with an appropriate load cell may be used.

Breaking strength retention (BSR) may be determined by in vitro degradation studies at pH 7.2 and 37° C., similar to in vivo conditions. The degradation profile may be obtained by measuring the percentage of the initial breaking strength over time.

The absorption profile may be determined in vivo via animal studies or in vitro with conditions similar to the in vivo environment. The material may be considered essentially absorbed when about 90% of the weight of the device is lost by in vitro testing or when the device and substantially all traces of the device have essentially disappeared in an in vivo study.

Particularly suitable polymers may include conventional bioabsorbable polymers such as polydioxanone, polyglycolide lactide-rich copolymers (e.g., 70%-90% lactide), or blends thereof, etc. Suitable absorbable polymers may be synthetic or natural polymers. Suitable biocompatible, bioabsorbable polymers include aliphatic polyesters, poly (amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof. For the purpose of this invention aliphatic polyesters include, but are not limited to, homopolymers and copolymers of lactide (which includes lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and polymer blends thereof. Natural polymers include collagen, elastin, hyaluronic acid, laminin, and gelatin, keratin, chondroitin sulfate and decellularized tissue. The kit devices of the present invention will preferably be made from the following bioabsorbable polymers: poly(p-dioxanone), co-polymers of poly(lactide-co-glycolide), and the blends thereof. However, any of the previously-mentioned polymers may be used in the kit devices of the present invention.

The term BSR or Breaking Strength retention as used herein is defined to have its conventional meaning, i.e., the breaking strength remaining in the device after a certain period of incubation in vivo or in vitro under a given set of conditions. The term bioabsorbable polymer as used herein is similarly defined to have its conventional meaning, i.e., polymer molecules that can degrade as a result of hydrolysis or interaction with bodily fluids, and which are eventually absorbed and/or excreted completely by the body after a certain period of time.

It is advantageous to keep the wall thicknesses of kit devices of the present invention relatively thin, while being sufficiently effective to maintain the functional and structural characteristics of the device, for example in the range of about 0.1 mm to about 0.6 mm. The advantages of thinner walls include relative ease of cutting or shaping the kit device to form nasal implant devices of different shapes or sizes. And, relatively thinner walls additionally provide for a lower mass of foreign material in a given implant area, which will provide benefits including to help decrease the likelihood of device extrusion, the sudden loss of integrity or support, or body/tissue reaction due to degradation products. The thinner walls are believed to result in an implant that is sufficiently strong and has advantages such as not increasing the natural anatomical width of the columella region.

As previously mentioned, the thickness of the kit devices of the present invention is sufficient to effectively provide the desired mechanical support characteristics of the devices cut from the kit. Typically, the wall thickness is between about 0.1 mm to about 0.6 mm, although the wall thickness may be thicker or thinner depending upon such factors as design, polymer selection, etc. The overall dimensions of the kit will be sufficient to effectively allow a surgeon to cut at least one nasal implant device from the kit, or large enough to cut multiple devices from the kit. The initial dimensions are typically sized larger than the actual size implanted in the patient so that the device may be customized or fitted by the surgeon to the patient by cutting or trimming the device intraoperatively prior to implantation. For exemplary purposes only, and not meant to be limiting, the kit devices may, for example, have a size of about 4 cm by 5 cm. Larger starting dimensions allow the surgeon to more easily manipulate the implant during preparation. The spacing between the outer walls of the kit devices of the present invention is sufficient to effectively contain tissue and/or provide spacing, for example, between about 1 mm to about 3 mm thickness.

The kit devices of the present invention can be made using conventional manufacturing processes including compression forming, injection molding, thermoforming, profile extrusion, and the like using conventional process equipment. The kit devices are preferably made as a single piece, but may be made from two or more pieces that are joined together using conventional techniques such as welding, gluing, mechanical fixation, etc. The devices of the present invention may be optionally coated (over the entire device or over one or more sections) with various conventional materials including bioabsorbable polymers, biologics, lubricants, therapeutic agents, active agents including antimicrobials, absorbable fibers including microfibers, combinations thereof and the like using conventionally coating processes. For example, coatings may be deposited on the surface by various conventionally known methods including spraying, dipping, immersion, lamination, electrostatic and the like using conventional coating equipment. A coating such as a thin layer of non-woven absorbable material, for example, melt-blown poly(p-dioxanone) nonwoven, can provide faster tissue ingrowth and more comfort to the patient. The coating materials may comprise therapeutic agents such as pharmacologically and/or biologically active agents, including, but not limited to, antibacterial agents, antimicrobial agents, growth factors, and wound healing agents. Active agents may include conventional therapeutic agents for treatment of pain and/or prevention of infection. Examples of active ingredients may include non-steroid anti-inflammatory drugs (NSAIDs) such as diclofenac sodium, indomethacine, ketoprofen, etc. Other types of active agents suitable to this invention may include conventional antibacterial agents such as triclosan and antibiotics.

Additionally, the kit devices of the present invention may be made from a bioabsorbable semi-rigid foam structure. The foam preferably has open and interconnected pores, although it may also have closed pores. The absorbable foam may be formed by any conventional method. For example, a gas or gas-forming agent may he added to absorbable polymer during or before being extruded to form a foam sheet. A water-soluble agent such as a salt may also be blended with an absorbable polymer to form a solid sheet first.

Conventional lyophylization processes may also be used to form the kit devices of the present invention. Those skilled in the art will appreciate that certain of the previously mentioned bioabsorbable polymers may be more useful to form foam structures than others, depending upon their individual characteristics and properties that make them useful in a foam forming process and the desired mechanical characteristics of the device. Some of the polymers that are useful to form foamed structures include poly(p-dioxanone), co-polymers of poly(lactide-co-glycolide) and the blends thereof.

One or more surfaces of the devices of the present invention may optionally have a specific surface roughness to facilitate fixation by increased friction and to create more favorable conditions for cell migration. The surface treatment can be provided in a variety of conventional manners, for example, during injection molding via the mold surfaces or in a surface blasting process similar to sand-blasting. Optionally, micro-pores or perforations of about 50-500 μm may be added throughout the surfaces to promote nutrition passage and tissue ingrowth. Biocompatible, bioabsorbable polymeric adhesives may also be provided on the kit devices of the present invention to assist in maintaining attached tissue to the implants, and to assist in placement of the implant devices in tissue, along with maintaining the position of the implants post-op.

The nasal kit devices of the present invention are packaged in conventional medical device packaging materials and packages in a conventional manner, and are delivered to the health care provider in a sterile condition. The kit devices are sterilized using conventional sterilization processes, including but not limited to ethylene oxide sterilization.

Figure 2:
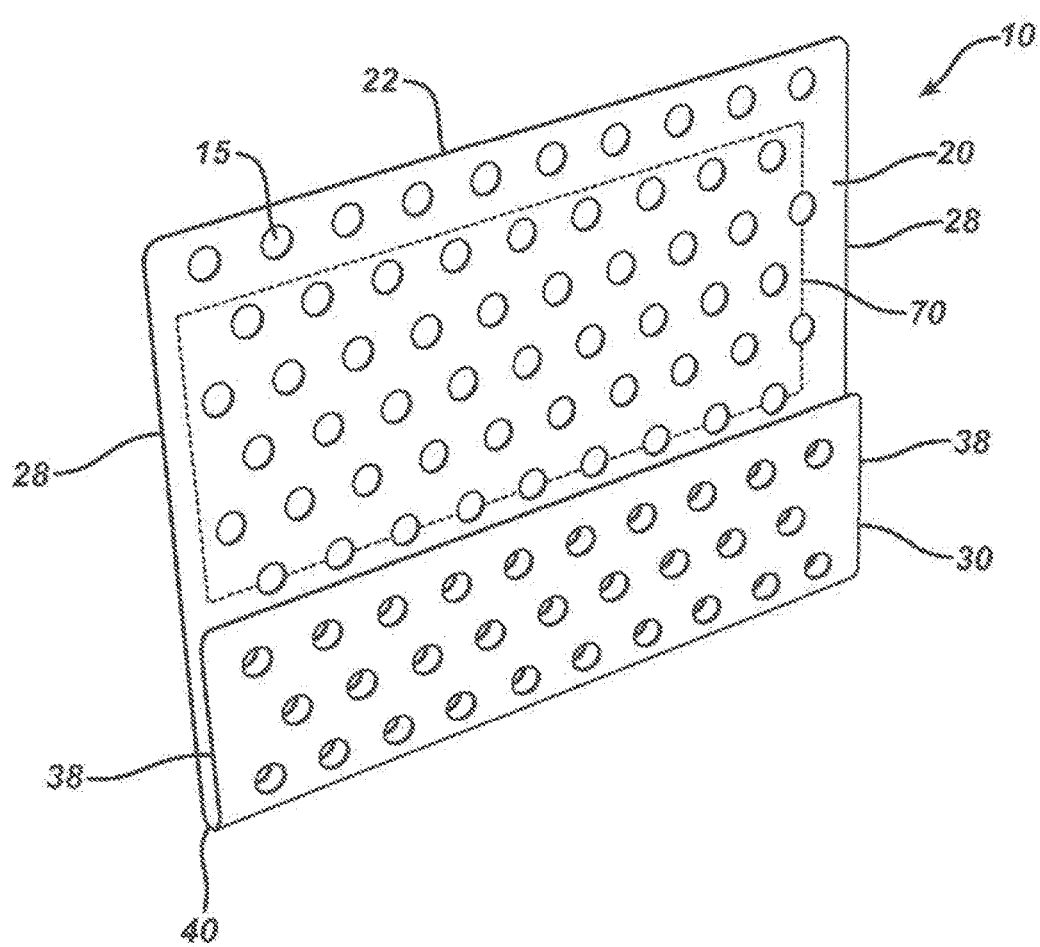
FIG. 2 is a perspective view of a universal kit device of the present invention useful to form a plate member; the kit device has an outline of the plate member.

Referring now to FIGS. 1 and 2, universal kit devices 10 of the present invention are seen. The kit device 10 is seen to have opposed wall members 20 and 30. Wall members 20 and 30 are seen to have a substantially rectangular shape but may have other geometric configurations, including but not limited trapezoidal, square, oval, etc., and may have opposed lateral ends that are straight or optionally rounded or curved. The wall members 20 and 30 preferably have openings or perforations 15, extending therethrough, but may also be solid if desired. The openings 15 are shown as having a circular cross-section, but may have any other geometric configuration, including oval, square, rectangular, polygonal, triangular, combinations thereof and the like. The openings 15 preferably extend through the wall members 20 and 30, but may also extend only partially into the wall members in a blind hole configuration. The openings 15 may cover all are part of the wall members 20 and 30. The wall members 20 and 30 are seen to have free top sides or outer edges 22 and 32, respectively. Wall member 20 has opposed lateral sides 28, and wall member 30 has opposed lateral sides 8. Wall member 20 has inner surface 25 and outer surface 27, and wall member 30 is seen to have inner surface 35 and outer surface 37. The wall members 20 and 30 are also seen to have bottom sides 24 and 34, respectively, connected by spine member 40. Spine member 40 is seen to be an elongated member having a curved cross-section, and having inner surface 42, outer surface 44, and opposed ends 46. Although it is preferred that spine member 40 have a curved cross-section, the spine member 40 may have other geometric cross-sections including rectangular, square, polygonal, etc. Bottom sides 24 and 34 of wall members 20 and 30 are connected preferably along their entire lengths to spine member 40 between ends 46 such that the wall members 20 and 30 are spaced apart from each other and are either parallel to each other or angulated with respect to each other. Alternately, the wall members may be attached along sections of bottom sides 24 and 34 to the spine member 40. The kit device 10 may be constructed as a single unitary member or the spine member 40 and wall members 20 and 30 may be manufactured as separate members and connected together or attached to form kit device 10 using conventional techniques including welding, gluing, mechanical fixation, etc. The spine member 40 acts in part as a base member so that the members 20 and 30 may partially rotate toward or away from each other to decrease or increase the size of opening 52. In other words, the wall members 20 and 30 have a first at rest position, and one or both members may be moved to a second position. However, although not preferred, and if one were willing to accept any disadvantages attendant therewith, the spine member 40 may also be designed to eliminate or substantially resist such movement. Although not illustrated, one or both of the wall members 20 and 30 may have a length that is greater than the length of the spine member 40. Conversely, the length of the spine member 40 may be greater. Also not illustrated is an embodiment of the present invention wherein the wall members 20 and 30 consist of segments separated by spaces, such that each segment is connected to the spine member 40. An embodiment of the device of the present invention (not illustrated) may have a segmented spine member connecting the walls 20 and 30, wherein the spine member segments are separated by spaces. As mentioned previously, it should be noted that if desired, spine member 40 may have other geometric cross-sections in addition to curved, for example, partially squared, polygonal, etc. The wall members 20 and 30 are seen to extend from or be connected to spine member 40. This may be accomplished by molding the spine member 40 and wall members 20 and 30 as a single unitary piece, or if the wall members and spine member are made separately, then the bottoms 24 and 34 may be connected or mounted to the spine member 40 in a conventional manner such as by welding, gluing, mechanical fixation, etc. Although in a preferred embodiment the wall members 20 and 30 are substantially flat, the wall members can be curved or otherwise non-planar.

The kit device 10 is seen to have channel 50 formed between the inner surfaces 25 and 35 and inner surface 42, extending along the length of the device 10. The device 10 has a longitudinal opening 52 formed between the outer edges 22 and 32, as well as opposed end openings 54. Opening 52 and end openings 54 are in communication with channel 50 in order to provide entry ways for tissue that may be contained partially or completely within channel 50 in certain implantable nasal devices that are cut from the kit 10. Openings 52 and 54 may expand or decrease corresponding to movements of wall members 20 and 30.

The wall members 20 and 30 are each seen to have a height. As illustrated in FIGS. 1 and 2, the height of wall member 20 is greater than the height of wall member 30, and this may be reversed if desired with wall member 30 having the greater height. Although not necessarily preferred, wall members 20 and 30 may have equal heights. Similarly, although it is preferred that the wall members 20 and 30 have equal lengths, the lengths may also differ.

The kit device 10 as illustrated in FIG. 2 is seen to have the outline 70 of a plate member 80 that may be cut from the kit. The outline may have a variety of other configurations for implantable nasal medical devices including plates, spreader graft members, columellar struts, nasal extension grafts, etc. The nasal implant devices may be cut by the surgeon or assistant in the field using conventional cutting apparatus including surgical scissors, scalpels, etc. The devices may be custom trimmed by the surgeon after cutting in a similar manner to provide a customized anatomical fit for the patient. Referring back to FIG. 1, the device is seen to have the outlines of several additional devices in addition to outline 70 for a plate member 80. The kit device 10 is also seen to have an outline 210 of a columellar strut device 200, and an outline 410 of a septal extension device 400, and an outline 510 of a spreader graft aid device 500. It is possible to cut all of these devices from a single kit device 10. The kit devices of the present invention may also be utilized without having an outline of one or more nasal implants devices. In such cases, the surgeon will cut the desired implant out from the kit device by either marking the kit in the field with an outline and then cutting, or simply cutting from memory.

Figure 3:
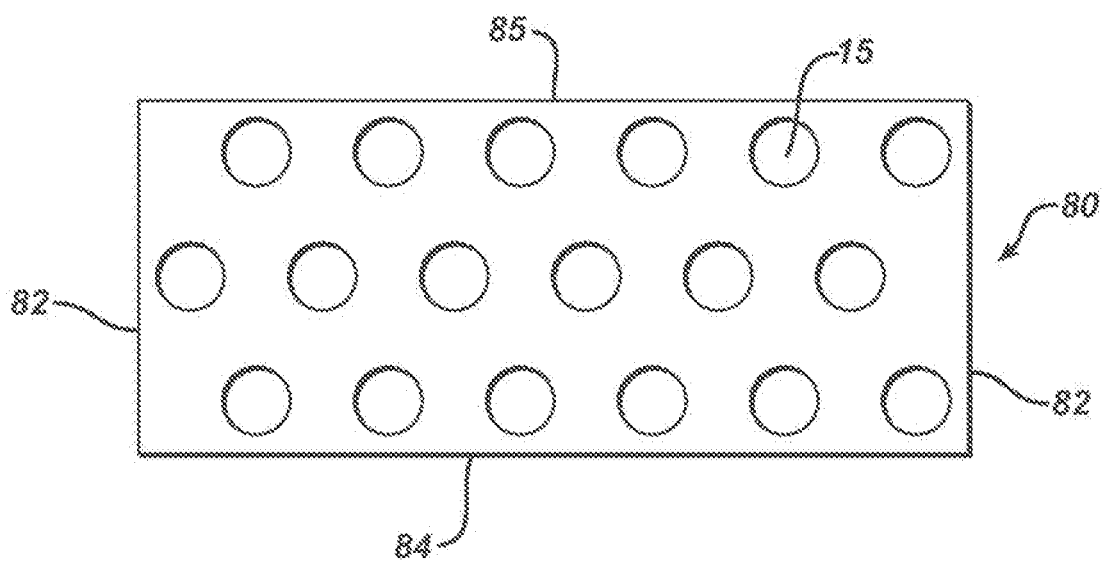
FIG 3 illustrates a plate member cut from the kit device of FIG. 2.

An implantable plate member 80 cut from the kit 10 is seen in FIG. 3. The plate member 80 is seen to have top side 85, and opposed sides 82 and bottom side 84 corresponding to the outline 70. Plate member 80 has openings 15. Such a plate member 80 can be used in a variety of nasal reconstruction surgical procedures, including, but not limited to, extracorporeal septal reconstruction, correction of septal deviation and stabilization of any cartilage grafts commonly used in septoplasty, and rhinoplasty procedures. The plate member 80 is typically shaped by the surgeon to conform to the nasal anatomy and the site of the desired reconstruction.

Figure 4:
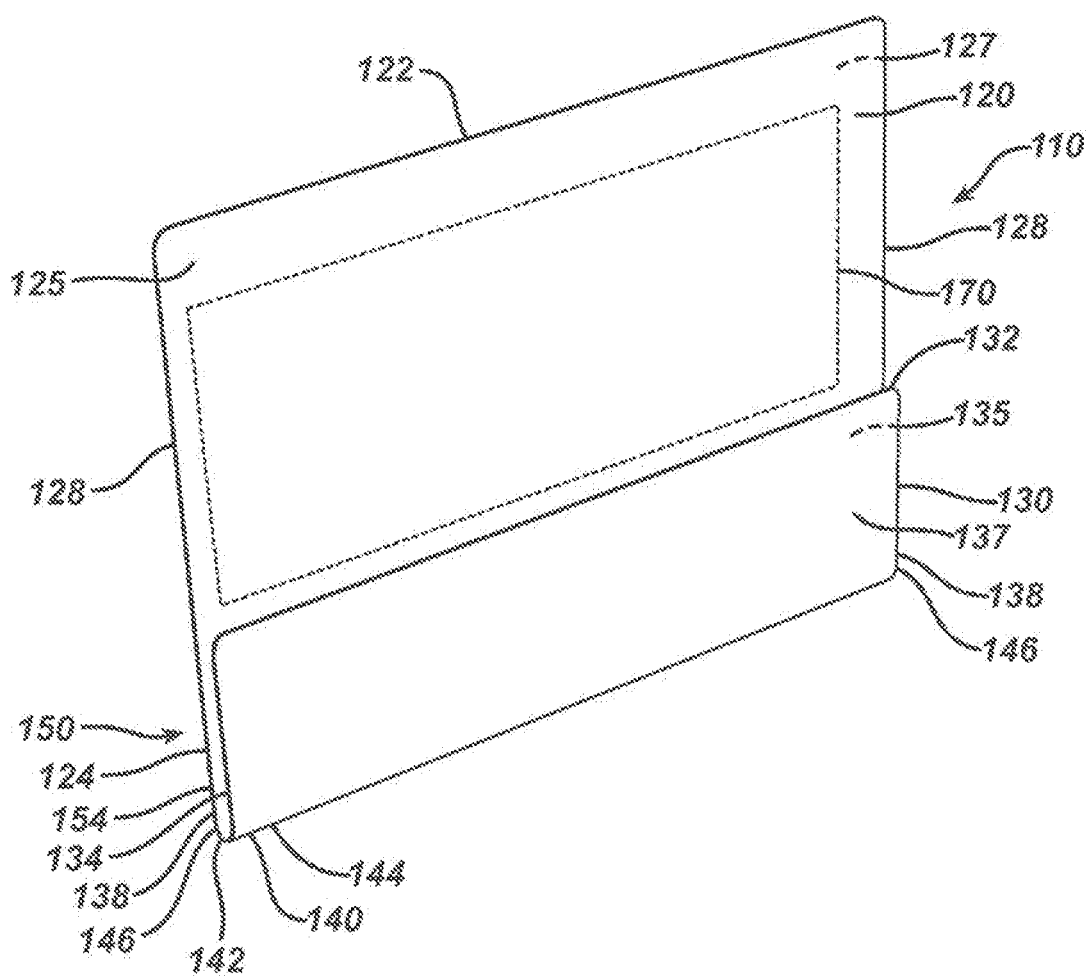
FIG. 4 is a perspective view of a non-perforated universal kit device of the present invention useful to form a plate member; the kit device has an outline of the plate member.

Referring now to FIG. 4, a non-perforated kit device 110 of the present invention is illustrated. The kit device 110 is seen to have opposed wall members 120 and 130. Wall members 120 and 130 are seen to have a substantially rectangular shape but may have other geometric configurations including but not limited trapezoidal, square, oval, etc., and may have opposed lateral ends or sides that are straight or optionally rounded or curved. The wall members 120 and 130 do not have openings or perforations, and are seen to be substantially solid. The wall members 120 and 130 are seen to have free top sides or outer edges 122 and 132, respectively. Wall member 120 has opposed lateral sides 128, and wall member 130 has opposed lateral sides 138. Wall member 120 has inner surface 125 and outer surface 127, and wall member 130 is seen to have inner surface 135 and outer surface 137. The wall members 120 and 130 are also seen to have bottom sides 124 and 134, respectively, connected by spine member 140. Spine member 140 is seen to be an elongated member having a curved cross-section, and having inner surface 142, outer surface 144, and opposed ends 146. Although it is preferred that spine member 140 have a curved cross-section, the spine member 140 may have other geometric cross-sections including rectangular, square, polygonal, etc. Bottom sides 124 and 134 of wall members 120 and 130 are connected preferably along their entire lengths to spine member 140 between ends 146 such that the wall members 120 and 130 are spaced apart from each other and either parallel to each other or angulated with respect to each other. Alternately, the wall members may be attached along sections of bottom sides 124 and 134 to the spine member 140. The kit device 110 may be constructed as a single unitary member or the spine member 140 and wall members 120 and 130 may be manufactured as separate members and connected together or attached to form kit device 110 using conventional techniques previously mentioned above. The spine member 140 acts in part as a base member so that the members 120 and 130 may rotate toward or away from each other to decrease or increase the size of opening 152 and the channel 150. In other words, the wall members 120 and 130 have a first at rest position, and one or both members may be moved to a second position. However, although not preferred, and if one were willing to accept any disadvantages attendant therewith, the spine member 140 may also be designed to eliminate or substantially resist such movement. Although not illustrated, one or both of the wall members 120 and 130 may have a length that is greater than the length of the spine member 140. Conversely, the length of the spine member 140 may be greater. Also not illustrated is an embodiment of the present invention wherein the wall members 120 and 130 consist of segments separated by spaces, such that each segment is connected to the spine member 140. An embodiment of the device of the present invention (not illustrated) may have a segmented spine member connecting the walls 120 and 30, wherein the spine member segments are separated by spaces. As mentioned previously, it should be noted that if desired, spine member 140 may have other geometric cross-sections in addition to curved, for example, partially squared, polygonal, etc. The wail members 120 and 130 are seen to extend from or be connected to spine member 140. This may be accomplished by molding the spine member 140 and wall members 120 and 130 as a single unitary piece, or if the wall members and spine member are made separately, then the bottoms 124 and 134 may be connected or mounted to the spine member 140 in a conventional manner such as by welding, gluing, mechanical fixation, etc. Although in a preferred embodiment the wall members 120 and 130 are substantially flat, the wall members can be curved or otherwise non-planar.

The kit device 110 is seen to have channel 150 formed between the inner surfaces 125 and 135 and inner surface 142, extending along the length of the device 110. The device 110 has a longitudinal or top opening 152 formed between the outer edges 122 and 132, as well as opposed end openings 154. Opening 152 and end openings 154 are in communication with channel 150 in order to provide entry ways for tissue that may be contained partially or completely within channel 150 in certain devices that are cut from the kit 110. Openings 152 and 154 may expand or decrease corresponding to movements of wall members 120 and 130.

The wall members 120 and 130 are each seen to have a height. As illustrated in FIG. 4, the height of wall member 120 is greater than the height of wall member 130, and this may be reversed if desired with wall member 130 having the greater height. Although not necessarily preferred, wall members 120 and 130 may have equal heights. Similarly, although it is preferred that the wall members 120 and 130 have equal lengths, the lengths may also differ.

The device 110 as illustrated in FIG. 4 is seen to have the outline 170 of a plate member 180 that may be cut from the kit. The outline 170 may have a variety of other configurations for implantable nasal medical devices including plates, spreader graft members, columellar struts, nasal extension grafts, etc.

Figure 5:
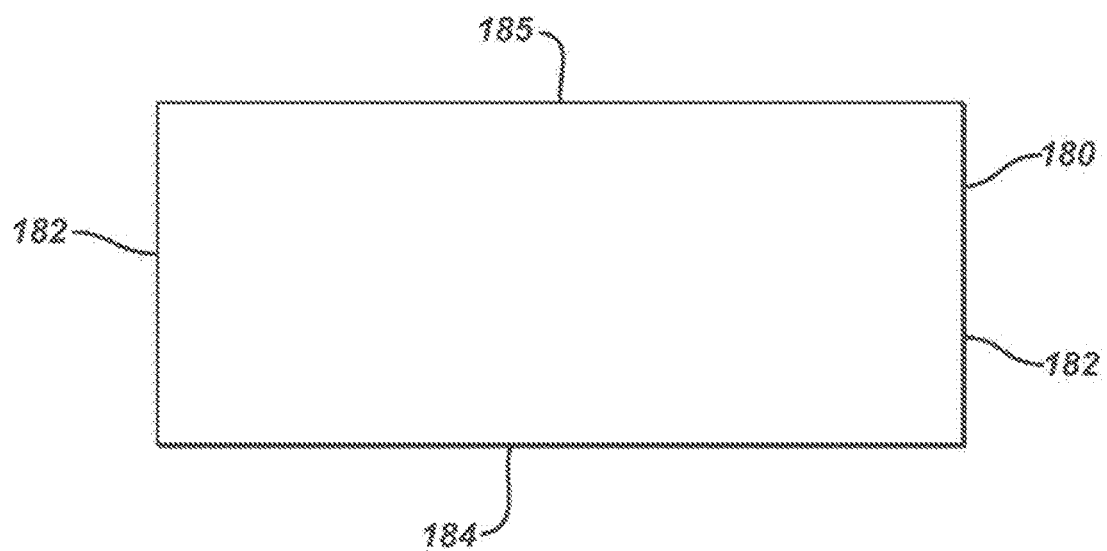
FIG. 5 illustrates a plate member cut from the kit device of FIG. 4; the plate member does not have perforations.

An implantable plate member 180 cut from the kit 110 is seen in FIG. 5. The plate member 180 is seen to have top side 185, and opposed lateral sides 182 and bottom side 184 corresponding to the outline 170. Plate member 180 does not have openings. Such a plate member 180 can be used in the nasal reconstruction surgical procedures previously mentioned for plate member 80, above.

Figure 6:
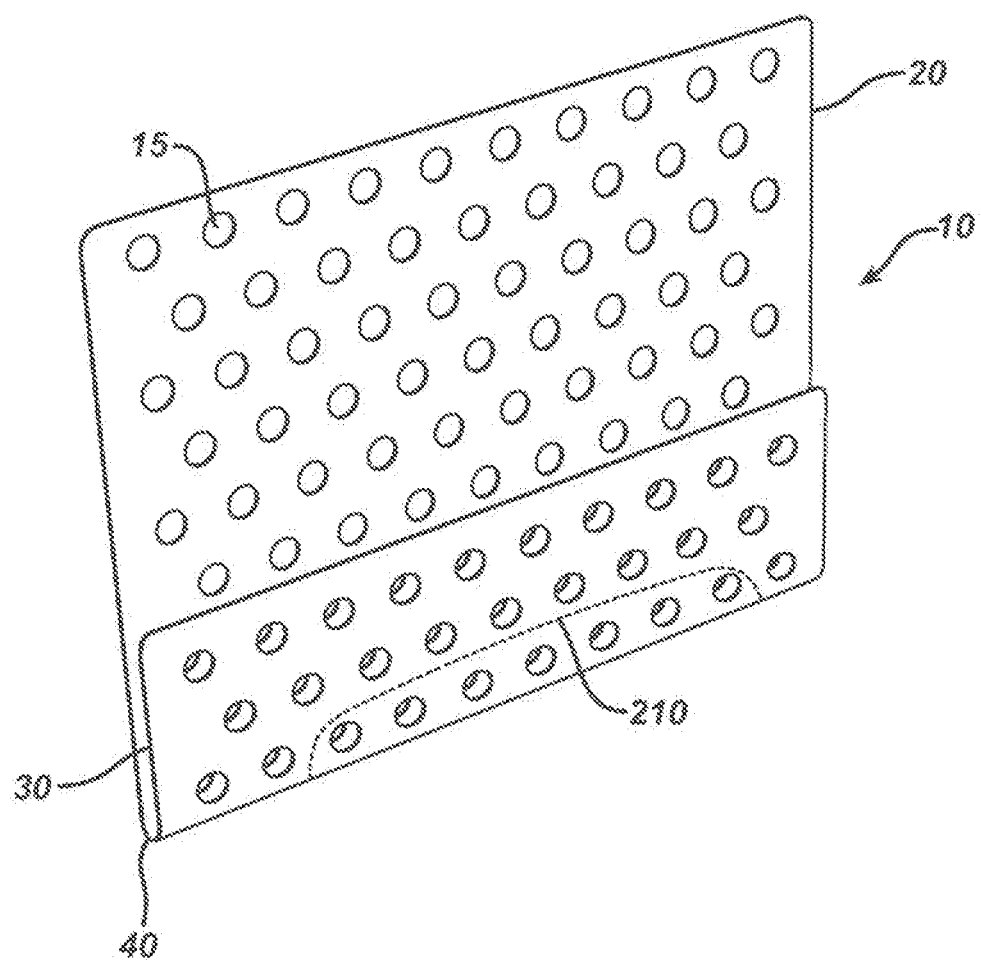
FIG. 6 is a perspective view of a universal kit device of the present invention useful to form a columellar strut; the device has an outline of the strut.
Figure 7:
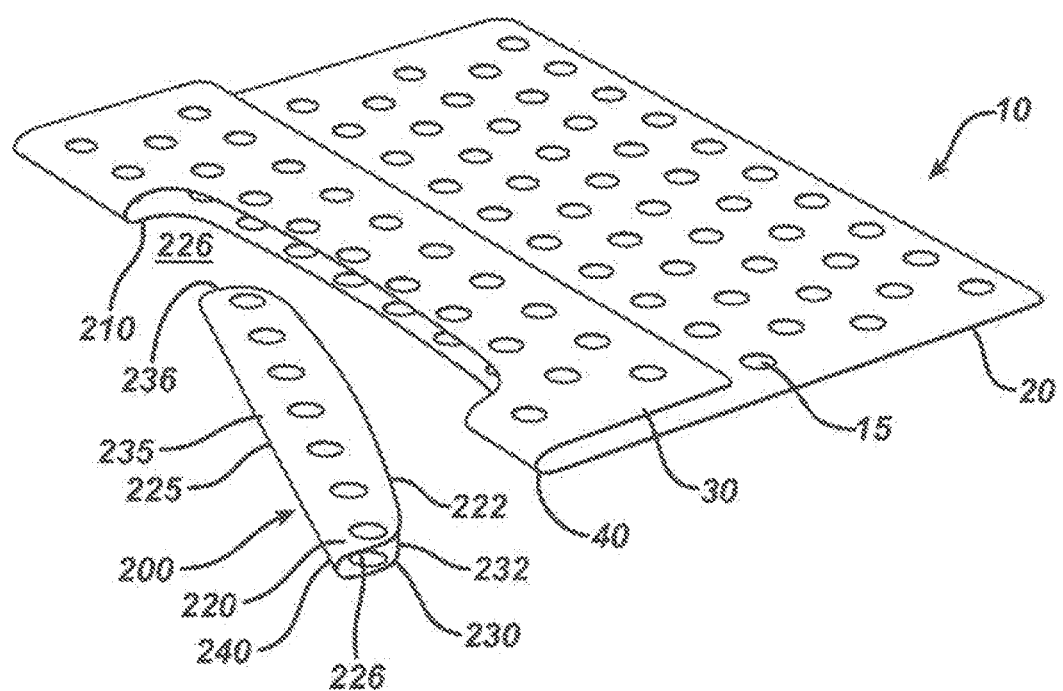
FIG. 7 is a perspective view of a columellar strut cut from the universal kit device of FIG. 6.

A kit device 10 of the present invention that can be used to make a columellar strut device 200 is seen in FIG. 6. The kit member 10 is seen to have opposed wall members 20 and 30 connected by spine member 40 as previously described. The kit member 10 illustrated in FIG. 6 is seen to have an outline 210 of a columellar strut device 200. Referring to FIG. 7, the columellar strut device 200 that has been cut from kit 10 along outline 210 is seen along side of the kit 10. The columellar strut is seen to have opposed side walls 220 and 230, having free top sides 222 and 232, bottom sides 225 and 235, and opposed ends 226 and 236, respectively. Spine member 240 connects the walls 220 and 230 along their bottom sides 225 and 235. The side walls 220 and 230, and spine member 240 define the inner channel 250 having top opening 252 and opposed end openings 254. The sidewalls 220 and 230 are seen to have optional openings 215.

Figure 8:
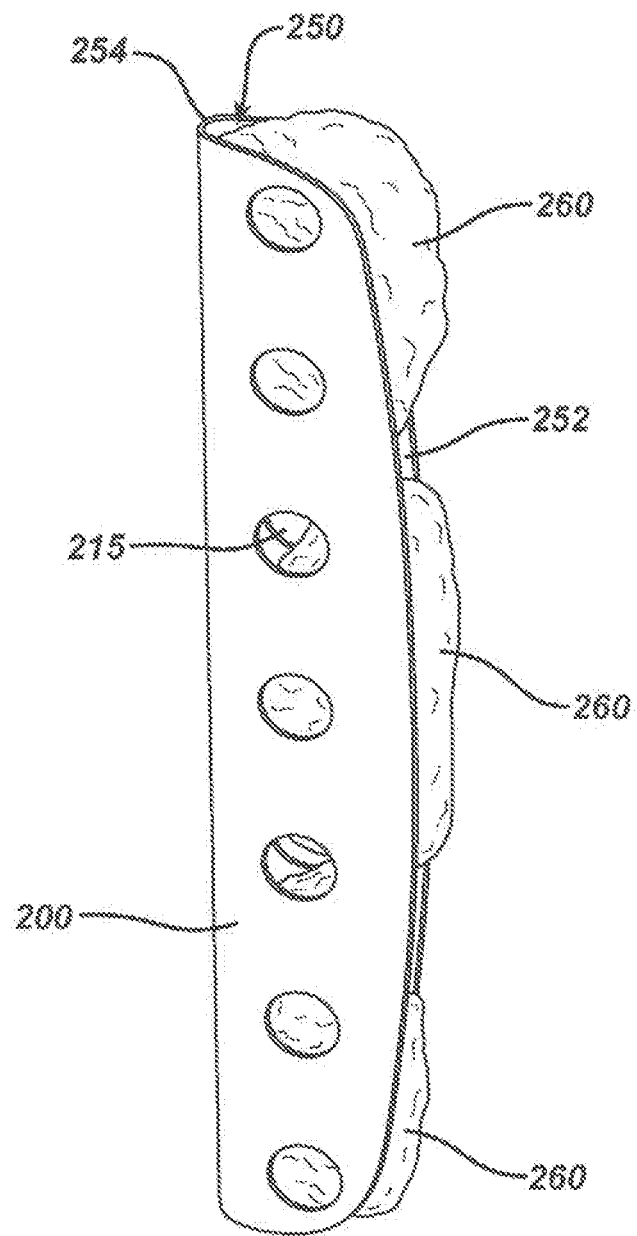
FIG. 8 is a perspective view of the columellar strut of FIG. 7 containing cartilaginous tissue.
Figure 9:
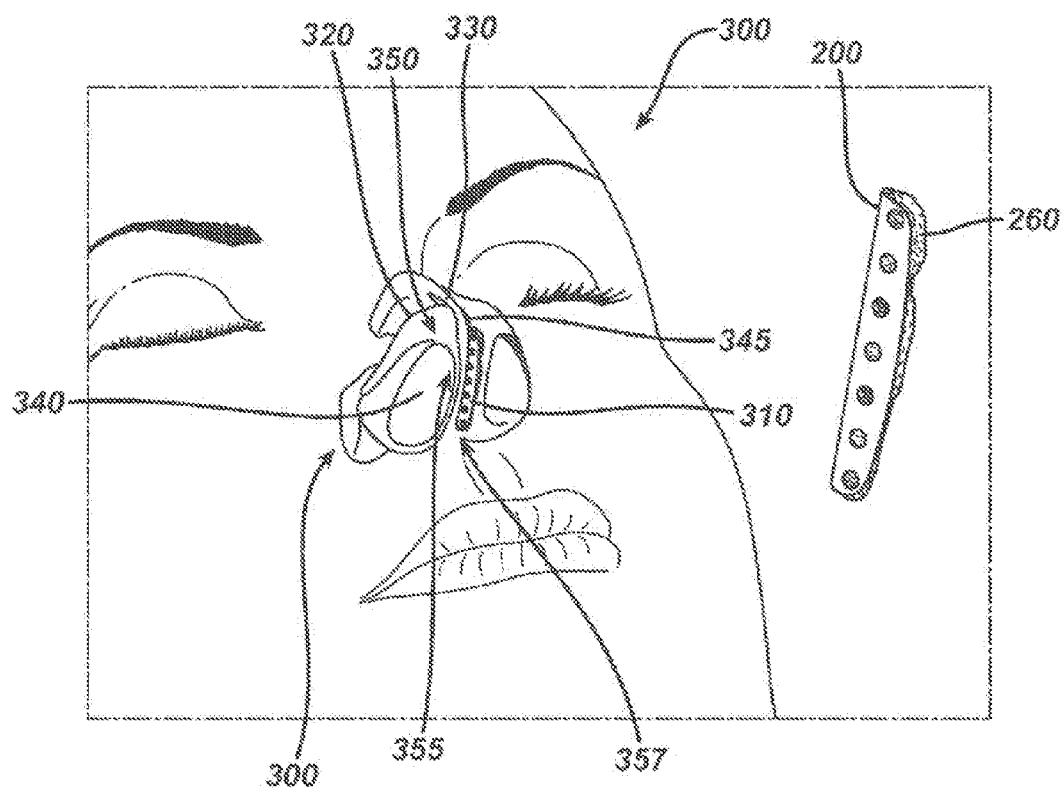
FIG. 9 illustrates the placement and positioning of the cartilage-filled columellar strut in a nasal surgical procedure.
Figure 10A:
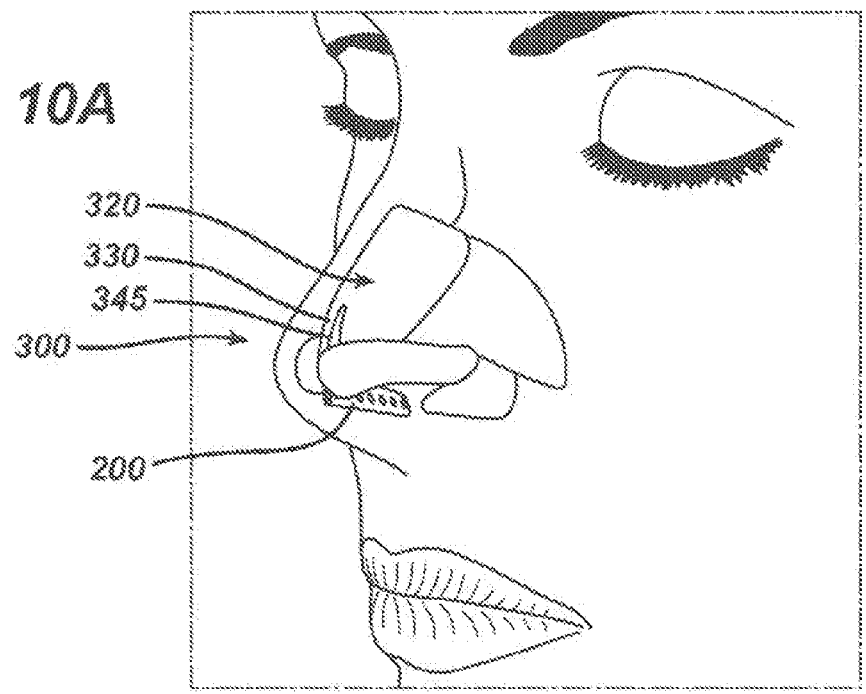
FIGS. 10A and 10B illustrated the columellar strut implanted in a patient's nose.
Figure 10B:
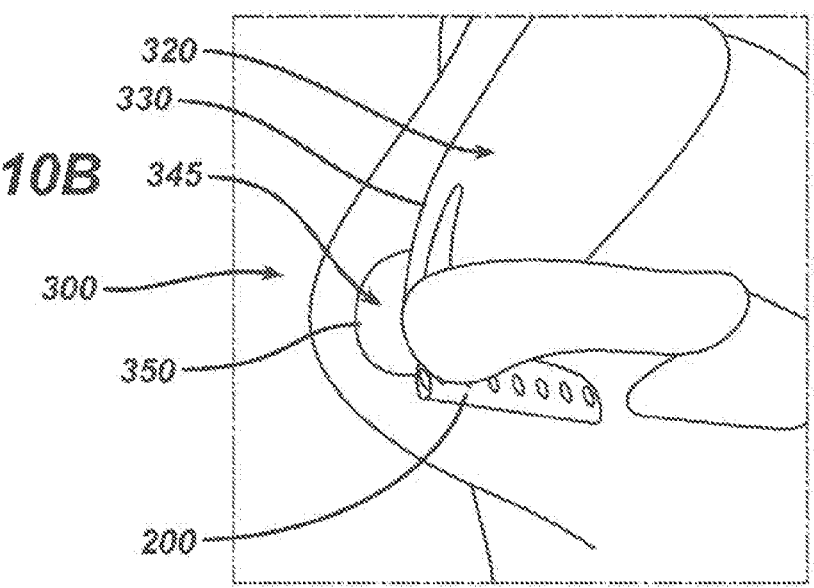

The columellar strut device 200 made from a kit 10 of the present invention is seen to be optionally loaded with cartilage 260 in channel 250 in FIG. 8, This is done prior to implantation by the surgeon, preferably using harvested autologous cartilage, although if desired allografts or synthetic bioabsorbable polymeric graft materials may be utilized. Sections of cartilage 260 may protrude out from channel 250 through top opening 252 and end openings 254 as illustrated if desired, or the cartilage 260 may be entirely contained within channel 250. The cartilage 260 may be optionally secured to device 200 in a conventional manner such as by suturing, gluing, stapling, tacking, etc. Referring to FIGS. 9, 10A and 10B, the cartilage-loaded strut 200 is seen to be implanted in a patient's nose 300. The nose 300 is seen to have the following structures, including the columella 310, the upper lateral cartilage structures 320, the septum 330, the nostrils 340, lower lateral cartilages 350 and the tip 345. The columellar strut device 200 containing cartilage 260 is implanted by the surgeon in the following manner. The connective tissue between the medial crus 355 of the lower alar cartilage 352 is separated to form a pocket that will allow the placement of an autologous graft or an implant. The columellar strut 200 is inserted in the pocket to the level of the nasal spine 357 or a higher position.

Figure 11:
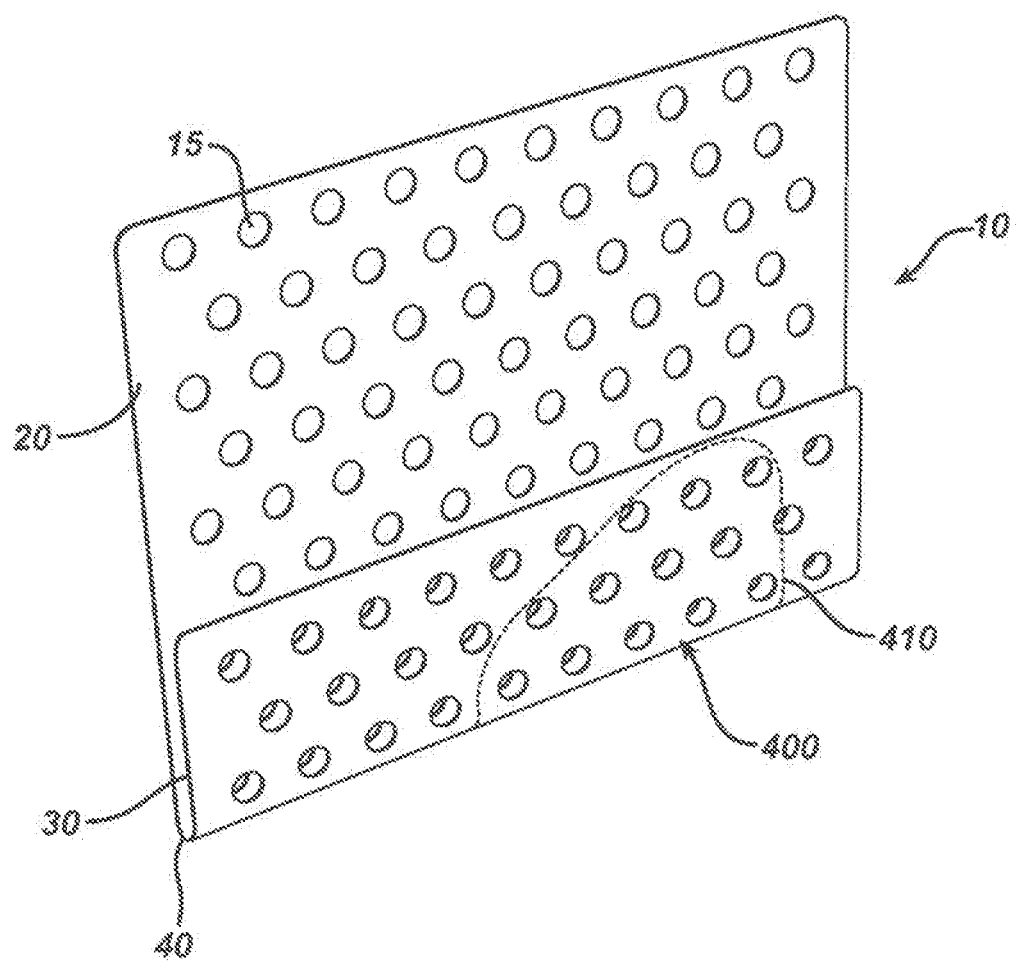
FIG. 11 is a perspective view of a universal kit device of the present invention useful to form a septal extension graft device; the kit device has an outline of the septal extension graft.
Figure 12:
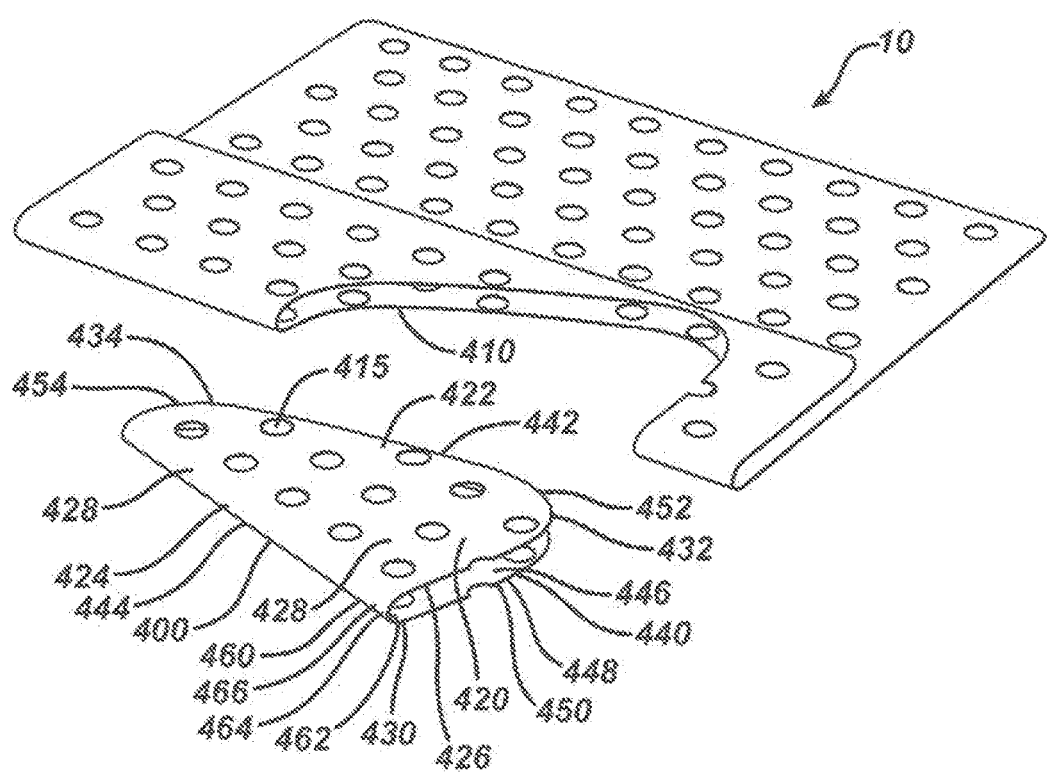
FIG. 12 is a perspective view of a septal extension graft device cut from the universal kit device of FIG 11.

A kit device 10 of the present invention that can be used to make a septal extension device 400 is seen in FIG. 11. The kit member 10 is seen to have opposed wall members 20 and 30 connected by spine member 40 as previously described. The kit member 10 illustrated in FIG. 11 is seen to have the outline 410 of a septal extension device 400. Referring to FIG. 12, the septal extension device 400 that has been cut from kit 10 along outline 410 is seen along side of the kit 10. The septal extension device 400 is seen to have opposed wall members 420 and 440. Wall member 420 has free top side 422 and bottom side 424, as well as inner surface 426 and outer surface 428. Wall member 420 has opposed lateral end sides 430. Free top side 422 is seen to slope from curved shoulder 432 to curved shoulder 434. The shoulders 432 and 434 connect free top side 422 to lateral end sides 430. Similarly, wail member 440 has free top side 442 and bottom side 444, as well as inner surface 446 and outer surface 448. Wall member 440 has opposed lateral end sides 450. Free top side 442 is seen to slope from curved shoulder 452 to curved shoulder 454. The shoulders 452 and 454 connect free top side 442 to lateral end sides 450. The wall members 420 and 440 are seen to have optional openings 415 extending through the walls. Spine member 460 is seen to have inner surface 462 and outer surface 464. The bottom ends 424 and 444 of wall members 420 and 440 are connected or attached to spine member 460 such that a cavity or channel 405 is defined between the inner surfaces 426, 446, and 462, having opposed end openings 407 and top side opening 409. The spine member 460 is seen to have a substantially semi-circular cross-section, but may have other geometric cross-sections as well.

The septal extension grafts 400 made from the kits 10 of the present invention may be implanted by the surgeon as illustrated in FIGS. 13-16. Initially, after forming, preferably by cutting, the septal extension graft 400 from the kit 10, cartilage 470 is placed within the channel 405 by the surgeon. The cartilage may be autologous cartilage harvested from a site on the patient, or an allograft or synthetic bioabsorbable polymeric graft. The cartilage 470 may be completely contained within channel 405 or may extend out through the end openings 407 and top opening 409. The cartilage 470 may be optionally secured to device 200 in a conventional manner such as by suturing, gluing, stapling, tacking, etc. As seen in FIGS. 13A and 13B, the wall members 420 and 440 may be completely or wholly conform to the outline 410, or sections of one or both of wall members 420 and 440 may be partially removed to reduce the mass of the implant. For example, as seen in FIG. 13B, sections of wall member 440 have been cut out leaving wall strut members 441 to contain the cartilage 470. Next, the cartilage-filled device 400 is implanted in a nose 300 in the following manner. The septal extension graft 400 is placed caudally and adjacent to the native septum 330 on one or both sides. The wall members 420 and 440 of septal extension graft 400 extend over the native septum 330. The cartilage pieces 470 attached to the septal extension graft 400 are positioned as close as possible to the native septum 330 to provide greater stability of the graft. One or both wall members 420 and 440 may be trimmed as desired by the surgeon to minimize the foreign body material load, e.g., trimming part of the wall member to leave only supporting strips or strut members 441 instead of leaving a complete wall member (See FIG. 13B).

Figure 17:
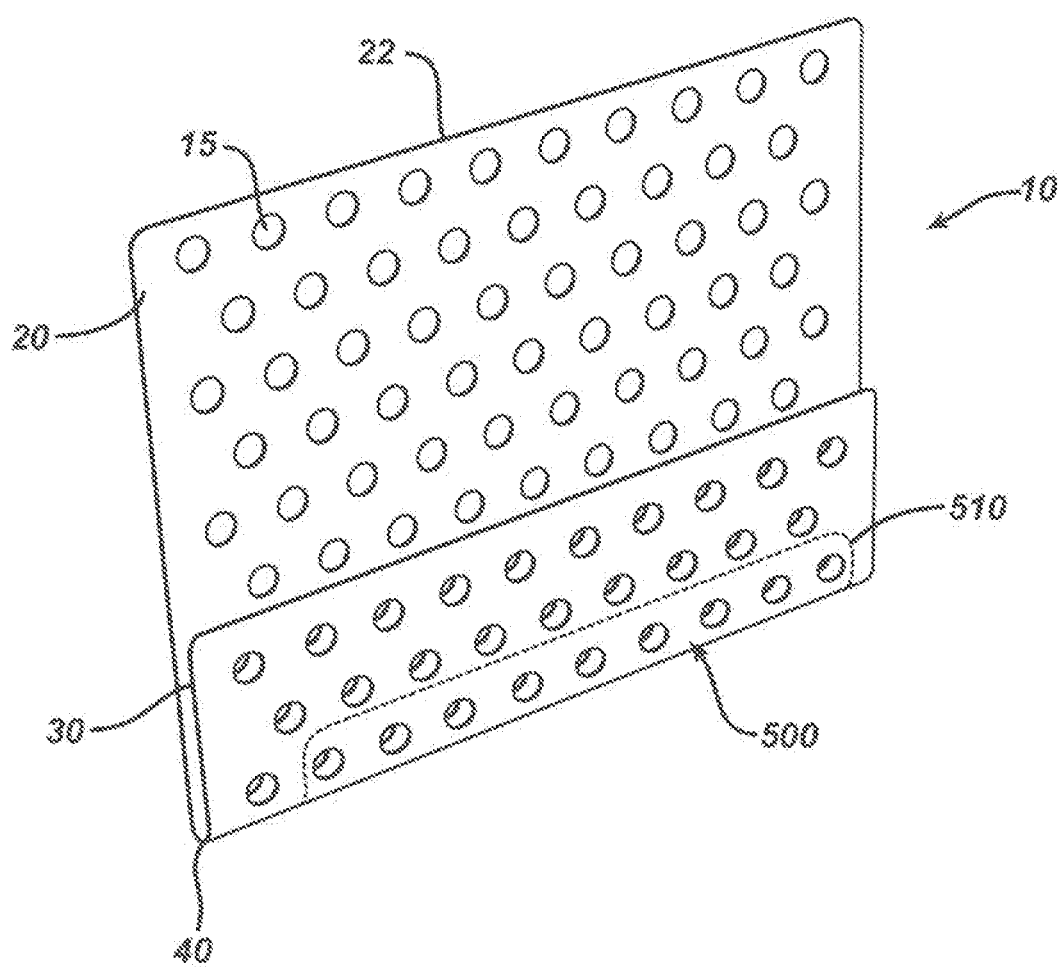
FIG. 17 is a perspective view of a universal kit device of the present invention useful to form a spreader graft device; there is an outline of the spreader graft device on the kit device.
Figure 18:
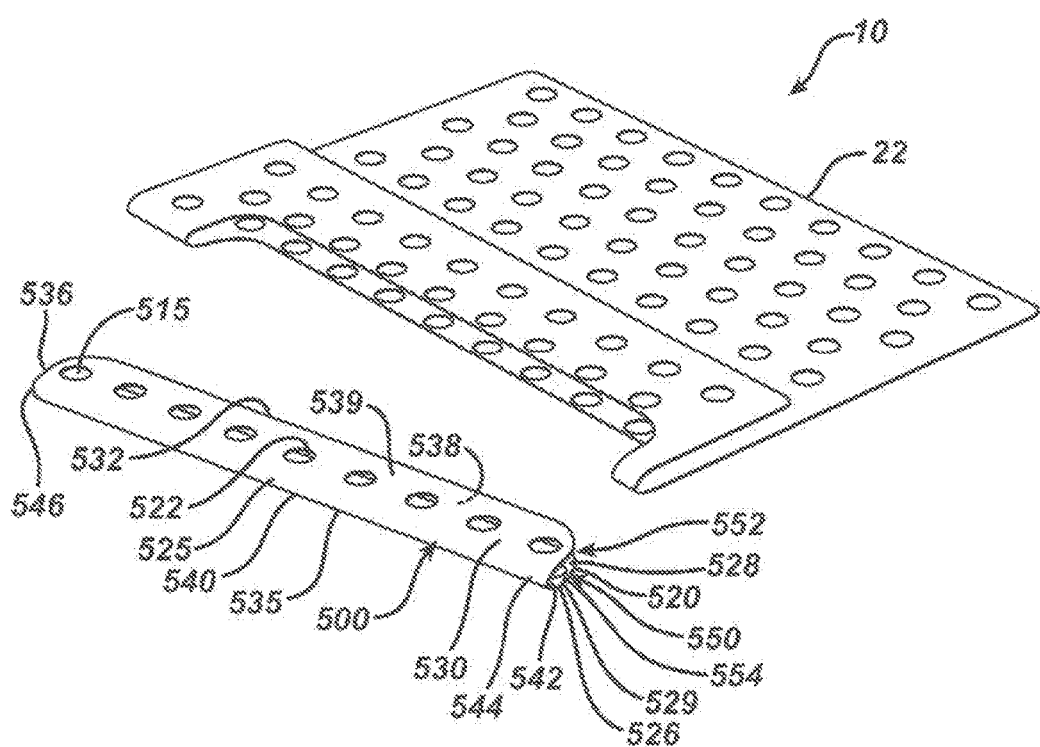
FIG. 18 is a perspective view of the spreader graft device cut from the kit device of FIG. 17.

A kit device 10 of the present invention that may be used to make a nasal spreader graft aid device 500 is seen in FIG. 17. The kit member 10 is seen to have opposed wall members 20 and 30 connected by spine member 40 as previously described. The kit member 10 illustrated in FIG. 17 is seen to have the outline 510 of a nasal spreader graft aid device 500. Referring to FIG. 18, the device 500 that has been cut from kit 10 along outline 510 is seen alongside of the kit 10. The spreader graft 500 is seen to have opposed side wall members 520 and 530, having free top sides 522 and 532, bottom sides 525 and 535, and opposed lateral end sides 526 and 530, respectively. Wall member 520 is seen to have inner surface 528 and outer surface 529. Wall member 530 is similarly seen to have inner surface 538 and outer surface 539. Spine member 540 connects the walls 520 and 530 along their bottom sides 525 and 535. Spine member 540 has inner surface 542, outer surface 544 and opposed lateral ends 546. Spine member 540 preferably has a generally curved cross-sectional configuration as illustrated, but may have other geometric configurations if desired. The side walls 520 and 530, and spine member 540 define the inner channel 550 bounded by inner surfaces 528, 538 and 542. Channel 550 is seen to have top opening 552 and end openings 554. The wall members 420 and 530 are seen to have optional openings 515 extending through the walls. The spine member 540 acts in part as a base member so that the wall members 520 and 530 may partially deform and rotate toward or away from each other to decrease or increase the size of opening 552 and the channel 550. However, although not preferred, and if one were willing to accept any attendant disadvantages, the spine member 540 may also be designed to eliminate or substantially resist such movement.

Figure 19:
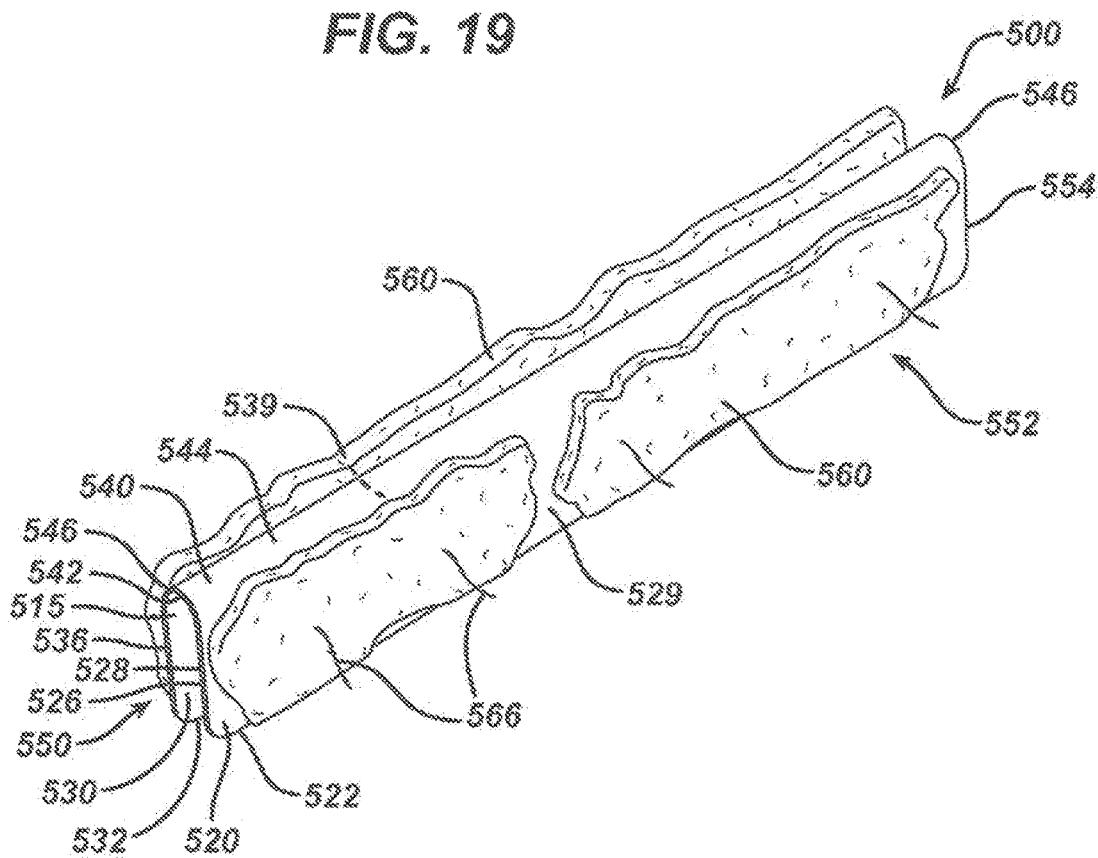
FIG. 19 illustrates cartilage mounted to the opposed outer surfaces of the spreader graft device.
Figure 20:
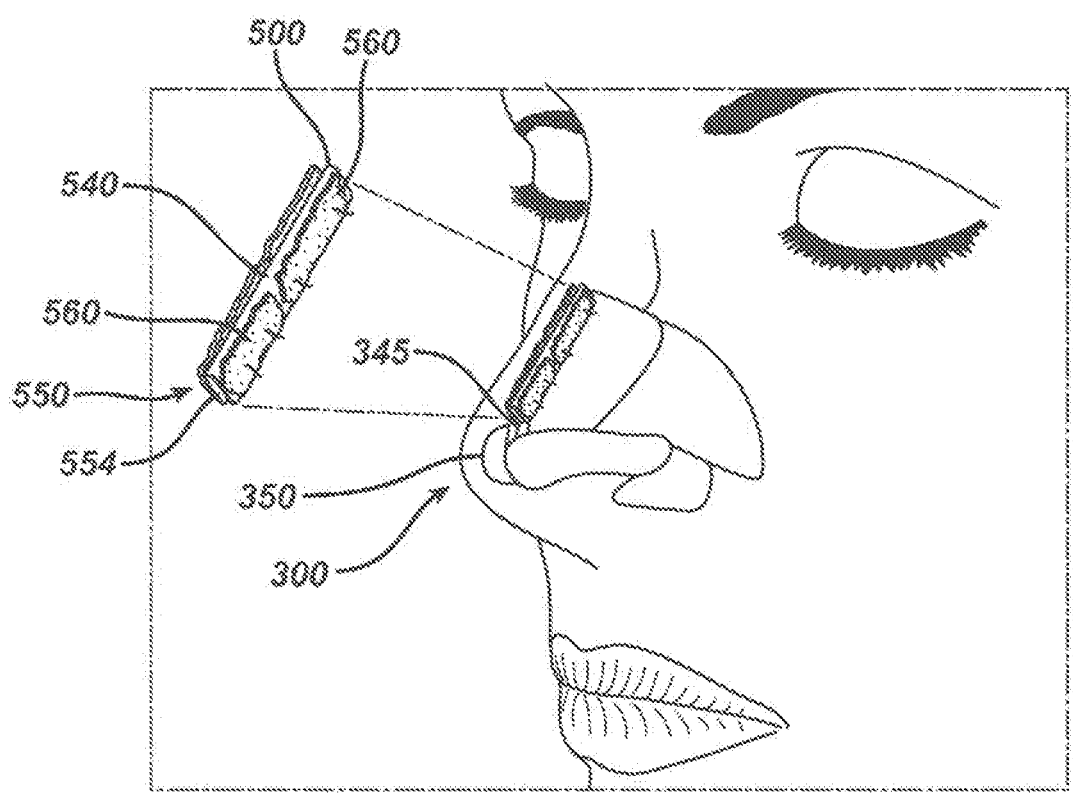
FIG. 20 illustrates the positioning of the spreader graft device in a patient's nose in a surgical procedure.

The spreader graft aid device 500 made from a kit 10 of the present invention is seen with mounted cartilage 560 in FIG. 19. Cartilage pieces 560 are mounted to the outer surfaces 529 and 539 in a conventional manner, preferably by using conventional sutures 566. The cartilage pieces 560 are mounted to outer surfaces 529 and 539 of the wall members 520 and 530. Referring to FIG. 20, the cartilage-loaded spreader graft 500 is seen to be implanted in a patient's nose 300. The spreader graft device 500 with mounted cartilage 560 is implanted by the surgeon in the following manner. After separating the lower lateral cartilage 350 and the upper lateral cartilage 320 in case of an open rhinoplasty procedure, the interior channel 550 of the spreader graft aid device 500 is placed on top of the native septum 330 as a saddle. The upper lateral cartilages 320 are approximated to the native septum 330 to restore the anatomy of the internal nasal valve.

Figure 21:
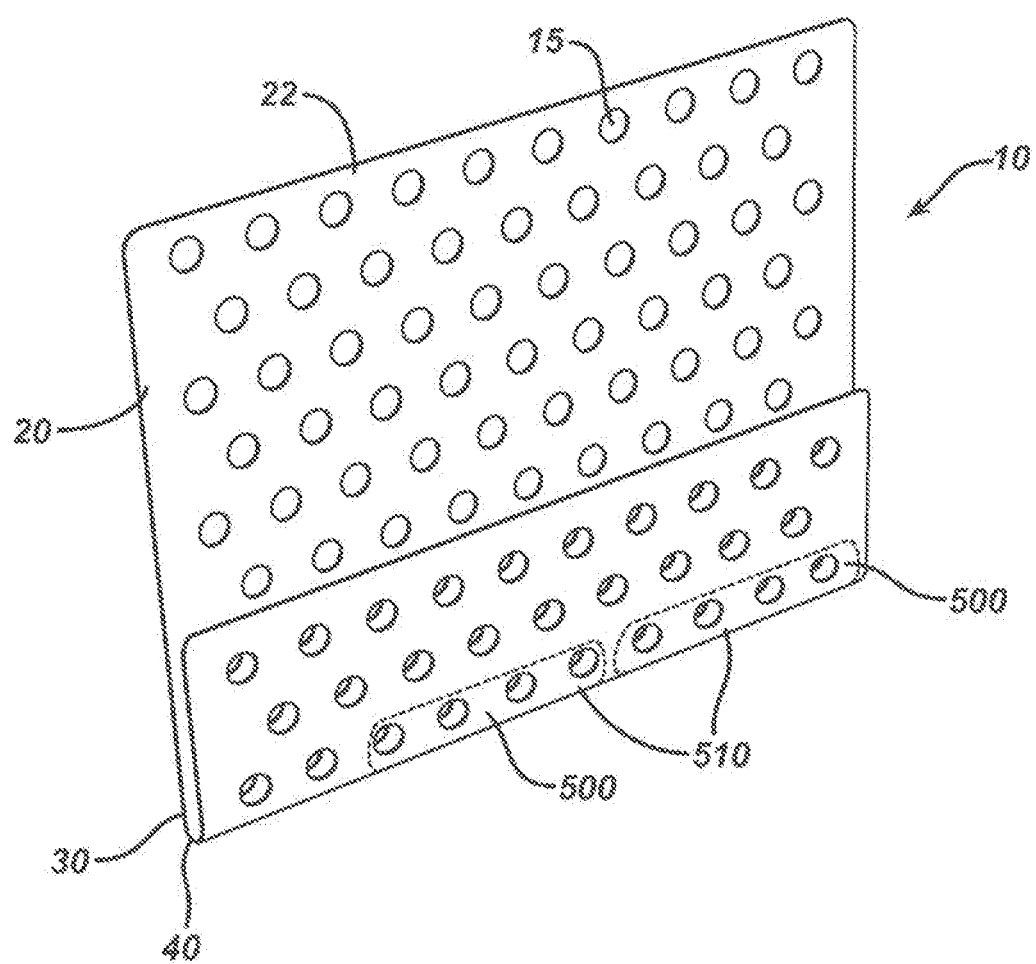
FIG. 21 is a perspective view of a kit device of the present invention useful to form multiple spreader grafts; an outline of each spreader graft is on the device.
Figure 22:
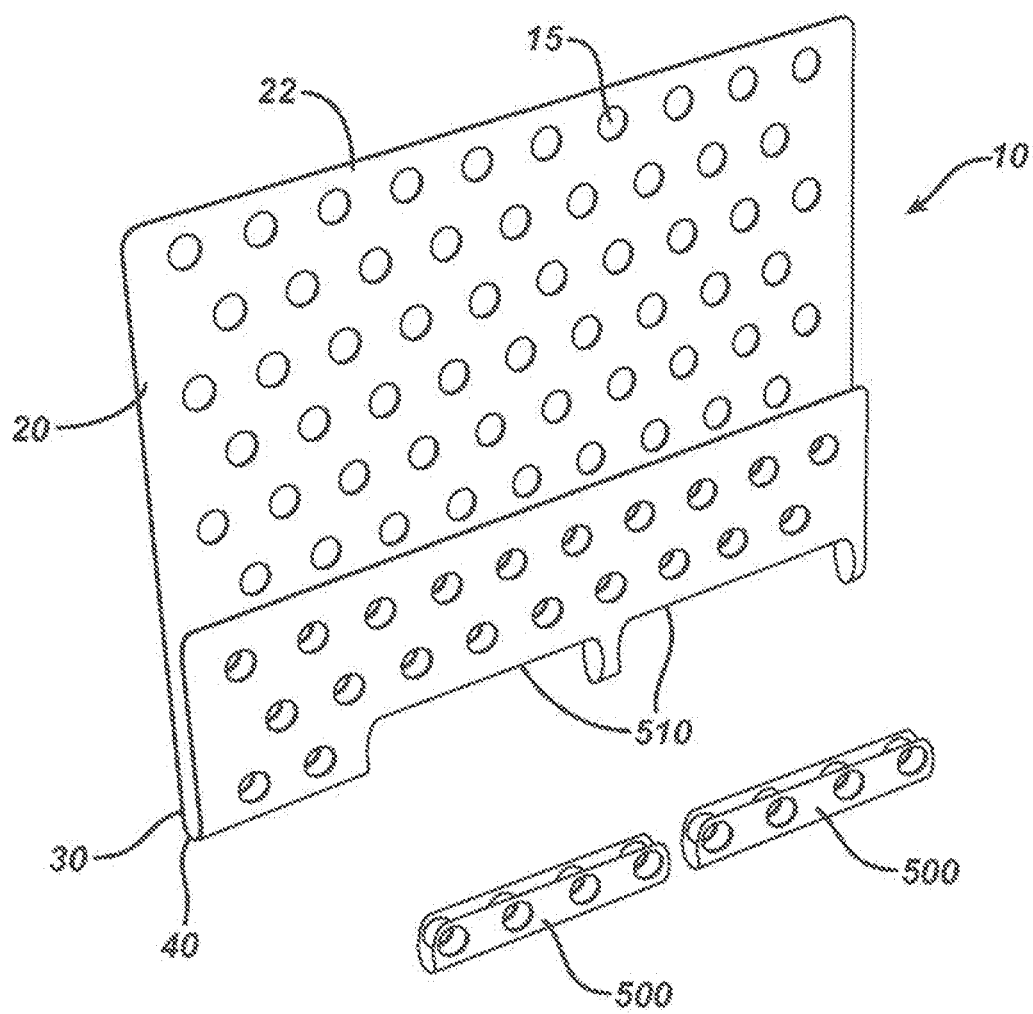
FIG. 22 illustrates two spreader grafts cut from the kit of FIG. 21.
Figure 23:
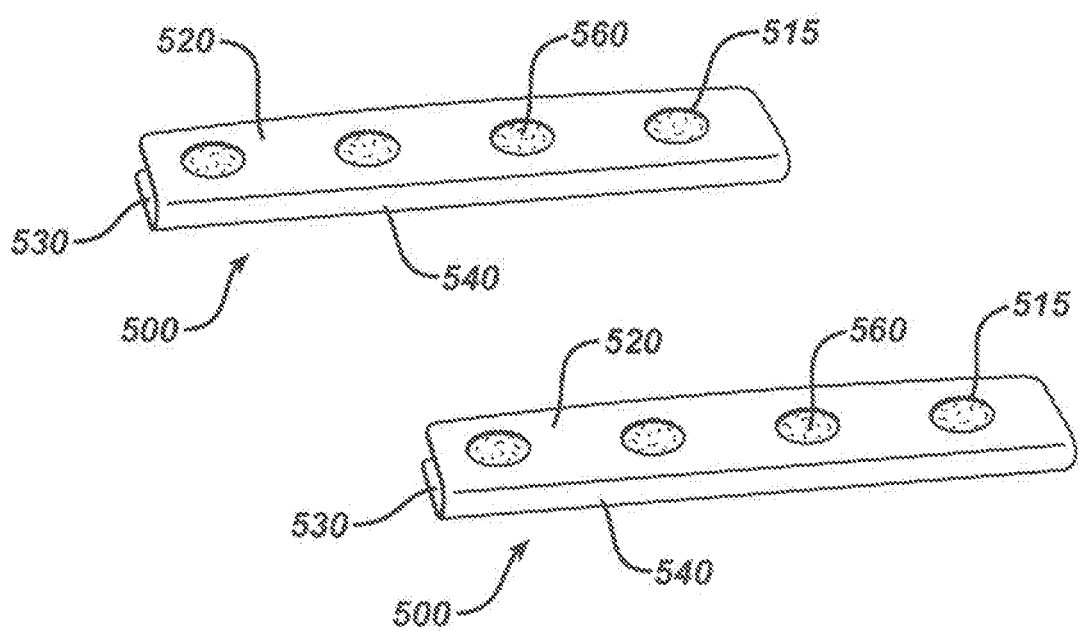
FIG. 23 is a perspective view of the spreader grafts of FIG 22.
Figure 24:
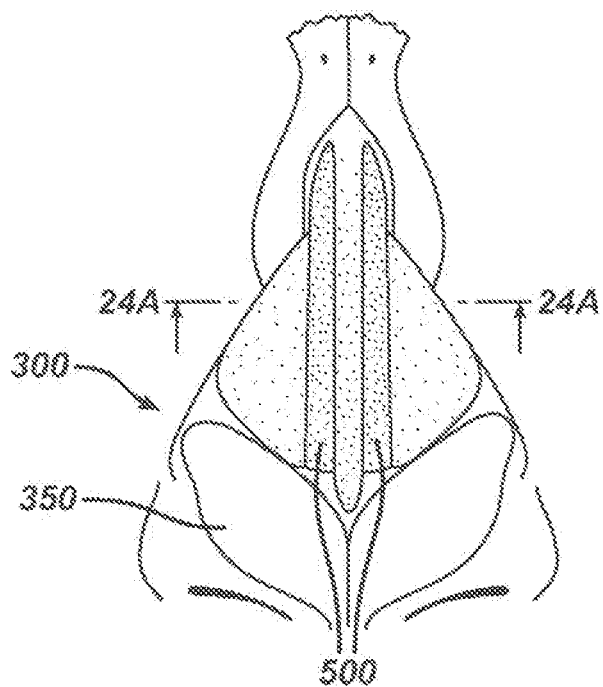
FIG. 24 is a schematic illustrating the spreader grafts implanted along opposite sides of a patient's nasal septum.
Figure 24A:
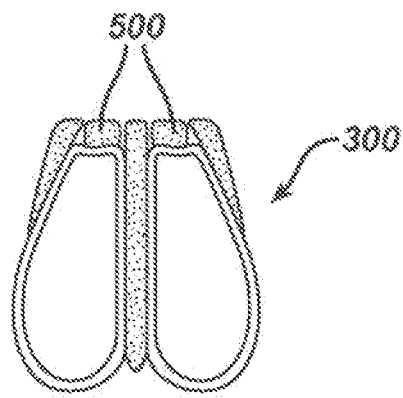
FIG. 24A is a cross-sectional view taken along View line 24A-24A illustrating the placement of the spreader grafts.

A kit device 10 that can be used to make two spreader graft aid devices 500 is illustrated in FIGS. 21-24. The kit member 10 is seen to have opposed wall members 20 and 30 connected by spine member 40 as previously described above. The kit member 10 illustrated in FIG. 21 is seen to have two outlines 510 of a nasal spreader graft aid device 500. Referring to FIG. 22, a pair of spreader graft aid devices 500 that has been cut from kit 10 along outline 510 is seen alongside of the kit 10. Both spreader grafts are seen in FIG. 23 and have the features and construction previously described above. The pair of spreader graft devices may be used in a nasal surgical procedure as schematically illustrated in FIG. 24 and FIG. 24A. In this approach, cartilage 560 is placed in the channels 550 adjacent or proximate to the inner surfaces 528, 538 and 542 and preferably maintained in position by conventional surgical sutures 566. Referring to FIG. 24, the cartilage-loaded spreader graft aid devices 500 are seen to be implanted in a patient's nose 300. The spreader graft aid devices 500 with cartilage inserts 560 are implanted by the surgeon in the following manner. The lower lateral cartilage 350 and upper lateral cartilage 320 are separated from the septum 330. When used in bi-lateral fashion, a spreader graft aid device 500 is placed on each side of the septum 330. The devices 500 are placed according to the currently used, conventional surgical technique and positioned so that the spine 540 of each device 500 extends not higher than the native septum 330. The devices 500 are secured to the native septum 330 in a conventional manner, such as by surgical sutures. The upper lateral cartilages 320 are approximated and secured to the native septum in a conventional manner to complete the reconstruction.

In the nasal surgical procedures previously discussed using the kit devices of the present invention, initially, a patient undergoing nasal reconstructive surgery is prepared for surgery in a conventional manner. Then a soft tissue envelope of the nose is elevated to gain access and visualization of the lower lateral cartilages. The soft tissue envelope consists of layers of soft tissue, muscle, and skin. Depending upon the type of reconstructive procedures being performed, one or more nasal implant devices of the present invention are cut from the kits, and more than one kit may be required for a particular procedure.

A typical rhinoplasty procedure may include one or more of the following steps, including elevation of mucpericondrial flaps, correction of airflow, elevation of soft tissue from bone or cartilage, obtaining cartilage grafting material, reshaping the dorsum, altering the nasal vault and placing various cartilage grafts such as radix, dorsal onlay, shield graft, alar batten, alar rim grafts, spreader grafts and columella strut graft. Using an open rhinoplasty approach as illustrated, a trans-columellar step incision is made. The soft tissue skin envelope is then dissected and elevated with a retractor. The surgeon prepares nasal implants from kit members of the present invention in the following manner. One or more desired implant outlines are cut from the kit device of the present invention and cartilage fragments are optionally secured to the side wall members, typically by using conventional sutures or other equivalent tissue securement devices and methods. The surgeon then implants the devices, e.g., columellar struts, plates, and spreader graft aids as follows. The locations of where the grafts are to be placed are identified, the surgical site is prepared by appropriate dissection and the implants are placed into position. The implants are fixated and held in place preferably with conventional surgical sutures. The preferred method of fixation is a horizontal mattress suture. Other conventional methods of surgical fixation may also be used including but not limited to adhesives, glues, tacks, staples and the like.

After the device is secured, or the multiple devices are secured, in place to the appropriate cartilaginous structures, the procedure is completed by redraping the soft tissue envelope over the nasal skeleton and then closing the columellar skin incision using surgical sutures or other conventional tissue approximation devices and techniques in a conventional manner.

The universal nasal kit devices of the present invention may be used to form a variety of nasal reconstructive implants. The implants include but are not limited to the following: columellar struts, plates, septal extension grafts, spreader grafts and alar batten grafts. In addition, customized implants having a variety of shapes may also be cut by the surgeon in the field from the novel universal kit devices of the present invention.

The outlines of nasal implants made from the kit devices of the present invention may be incorporated into or onto the kit devices in a variety of conventional manners including but not limited to printing, marking, cutting, scoring, hot pressing or thermal forming and the like and equivalents thereof.

The novel universal nasal kit devices of the present invention may be used in a variety of conventional nasal reconstruction surgical procedures and associated procedures involving cartilage reconstruction. These procedures include but are not limited to the following: septoplasty and rhinoplasty.

Nasal implants are cut by the surgeon or the surgeon's assistant from the novel kit devices of the present invention in the following manner. The desired implant contour outline is located on the kit sections for the outline form of the desired implant device. The outline of the desired implant is cut by surgical scissors or scalpel or any conventional cutting instrument. Any sharp edges on the cut device can be further trimmed. The contour may be further trimmed and shaped to account for proper sizing and placement in the nasal anatomy.

The following examples are illustrative of the principles and practice of the present invention although not limited thereto.

EXAMPLE 1

A universal nasal kit device of the present invention was thermally formed from a flat polymeric sheet made from a blend of 20 wt. % polydioxanone polymer and 80 wt. % of a copolymer of 85/15 poly(lactide-co-glycolide). The plate was extruded using a 1.25 inch extruder and a 10 inch flex lip film die, and collected on a three-roll horizontal stack with release papers on both side of the film. The extruder and the film line were manufactured by Crompton Davis Standard Corporation, Pawcature, Conn., USA. The film die had a temperature of about 185° C. and a die gap of 0.0.15 in. The turn was collected at a roll speed of about 1.5 feet per minute. The plate had a thickness of about 0.15 mm. Strips of the film were punched to produce perforations and the outline of the device. The plate had a width of 50 mm and a length of 56 mm. Multiple rows of suturing holes of about 2.0 mm in diameter were formed along a first line about 3 mm away from the centerline of the spine and the parallel lines of about 4 mm from each other throughout the flat portions of the kit device. The holes spaced about 4 mm from each other on a given line, were formed by die cutting. In a subsequent step the pre-cut devices were placed in a forming set of dies at about 70° C.-75° C. and formed in a U-shape configuration at one end of the kit device. The formed kit devices were then placed in a fixture to be annealed with an annealing cycle of heating from room temperature to about 60° C., held at this temperature for about 8 hours, then heated to about 70° C. for 4 hrs, then about 80° C. for 8 hours, and finally cooled down to the room temperature for a period of about 11-13 hrs in a Nitrogen atmosphere.

EXAMPLE 2

A universal nasal kit device of the present invention was thermally formed from a flat polymeric sheet made from a 100% polydioxanone polymer. The plate was extruded using the same equipment as described in Example 1. The film die temperature was set at about 140° C. and a die gap of 0.006 in. The film was collected at a roll speed of about 0.9 feet per minute. The plate had a thickness of about 0.25 mm. Strips of the film were punched to produce perforations and the outline of the device. The plate had a width of about 50 mm and a length of about 56 mm. Multiple rows of suturing holes of about 2.0 mm in diameter were formed along a first line about 3 mm away from the centerline of the spine and the parallel lines about 4 mm from each other throughout the remaining flat portions of the kit device. The holes spaced about 4 mm from each other on a given line, were formed by die cutting. In a subsequent step the pre-cut devices were placed in a forming set of dies at about 85° C. for a sufficiently effective time, and formed into a U-shape configuration at one end of the kit device. The formed devices were then placed in a fixture and annealed at about 85° C. for an additional 8-16 hours in a nitrogen atmosphere. Alternatively, the plate may also be folded with an appropriate folding device fixture at room temperature. Then, with the folded plate in the folding device fixture, it is heat set and annealed in the device fixture in one-step at about 85° C. for a total of 8-16 hours in a nitrogen atmosphere.

EXAMPLE 3

A patient has as a middle vault deficiency with resulting significant functional and cosmetic implications. The condition requires surgical intervention and repair. The patient is prepared for nasal reconstructive surgery in a conventional manner including the steps of injecting a local anesthetic, making marginal and/or columellar incisions, elevation of the soft tissue skin envelop and developing appropriate dissection planes. The procedure is continued by placing appropriate grafts and using suture techniques to achieve the desired functional and aesthetic results depending on the preoperative assessment and surgical plan. A spreader graft device of the present invention, having a configuration as seen in FIGS. 18 and 19, is cut from a kit device of the present invention as seen in FIG. 17 (and trimmed if required) and is implanted by a surgeon in the following manner: gaining access to the nasal dorsum; separating the upper lateral cartilages from the nasal septum; developing muchoperichondrial flaps at the junction of the septum and the ULC; placing the spreader graft device and, fixating the spreader graft device to the septum and the ULC.

Alternatively, the spreader graft device is placed by an endonasal approach by developing a tight subperichondrial pocket between the upper lateral cartilages and the septum and tunneling the spreader graft device in the pocket.

In order to provide adequate nasal tip support, the patient needs a columellar strut implant. A columellar strut device of the present invention having a configuration as seen in FIGS. 7 and 8 is cut from a kit device of the present invention as seen in FIG. 6 (and trimmed as necessary) and is implanted by the surgeon in the following manner: the lower lateral cartilages are separated and a pocket between the medial crus is developed. The implant is placed in the pocket and secured in place.

If no other grafts or structure modifications are required, the procedure is completed by re-draping the soft tissue over the nasal structure and closing the marginal and columellar incision.

EXAMPLE 4

Figure 13A:
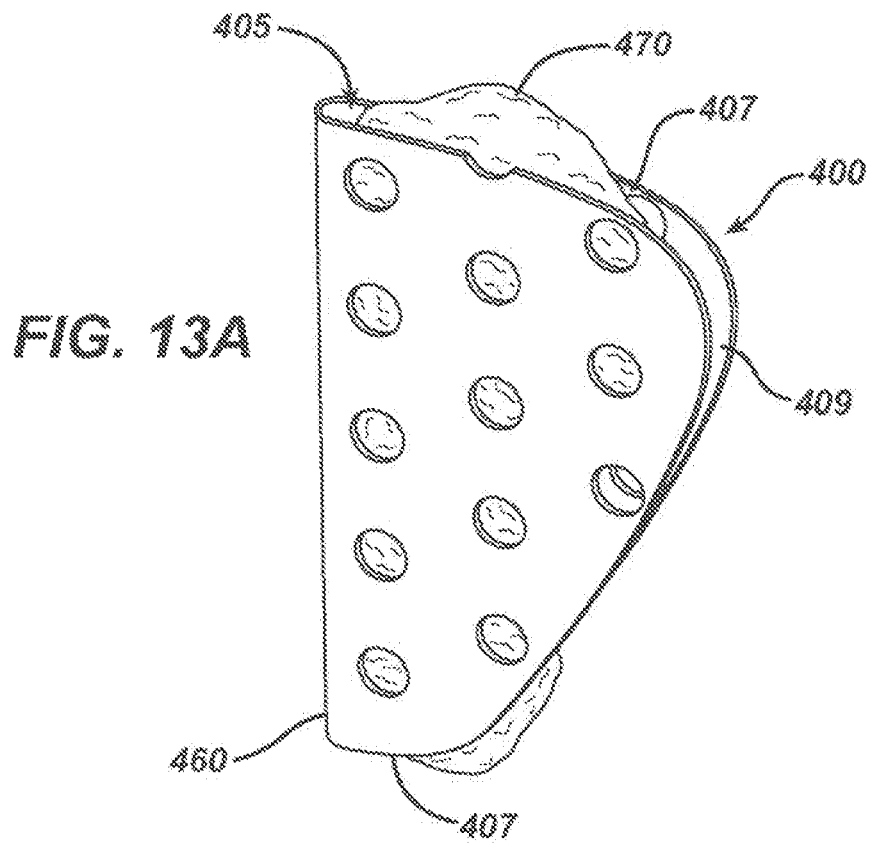
FIGS. 13A and 13B are perspective views of the septal extension graft filled with cartilaginous tissue.
Figure 13B:
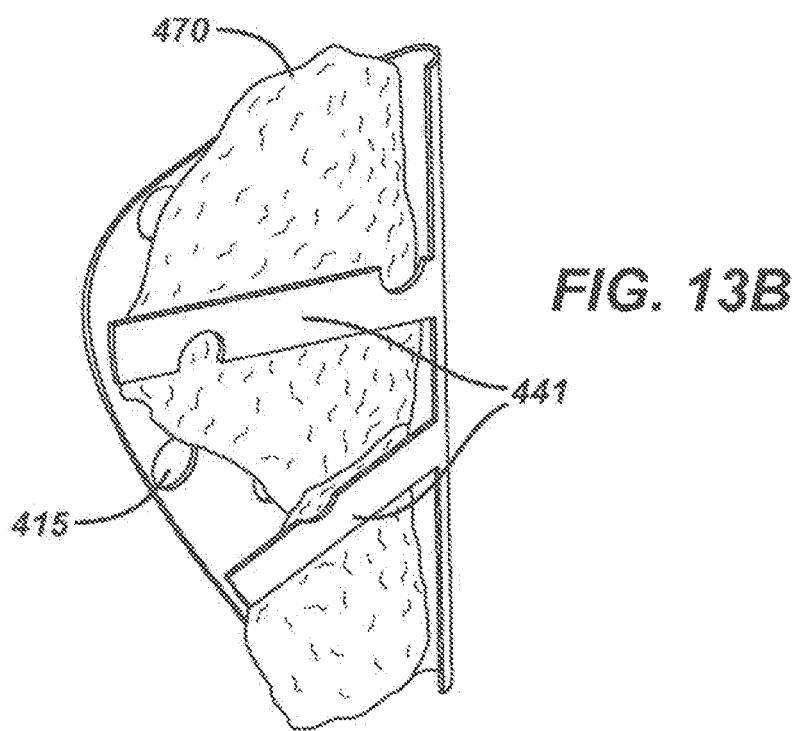
Figure 14:
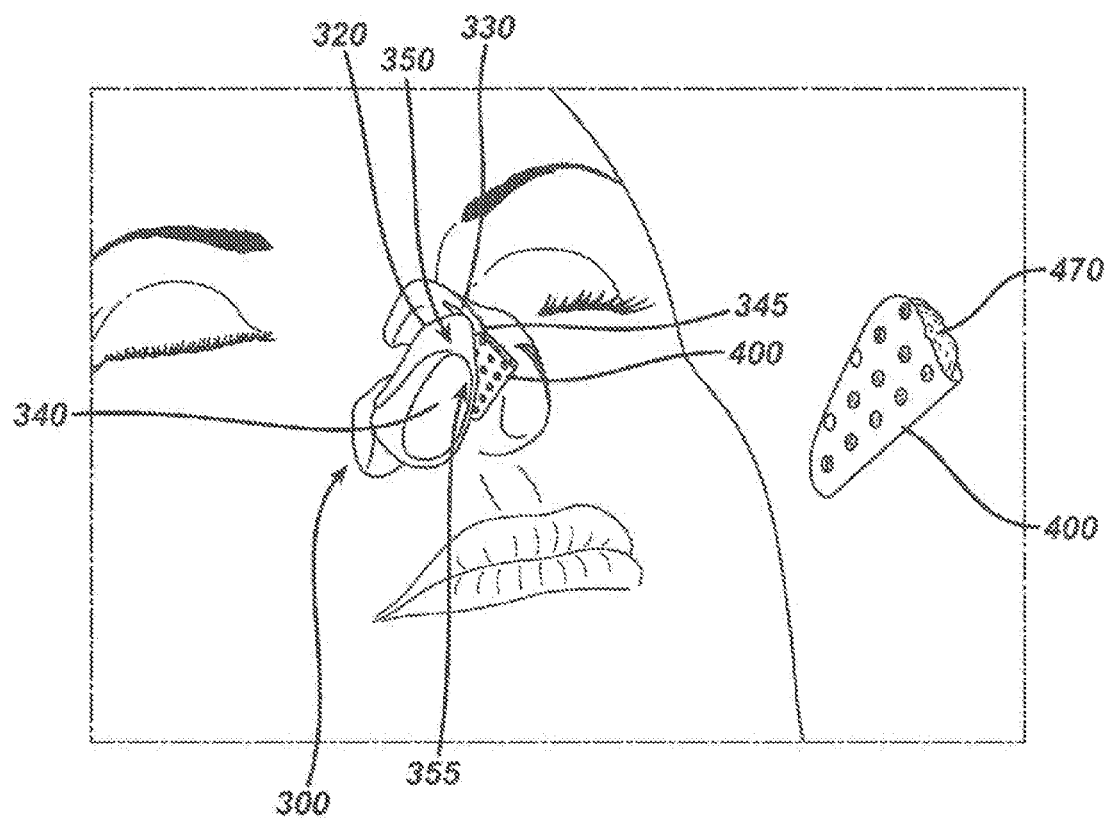
FIG. 14 illustrates the positioning of the septal extension graft in a patient during a surgical procedure.
Figure 15:
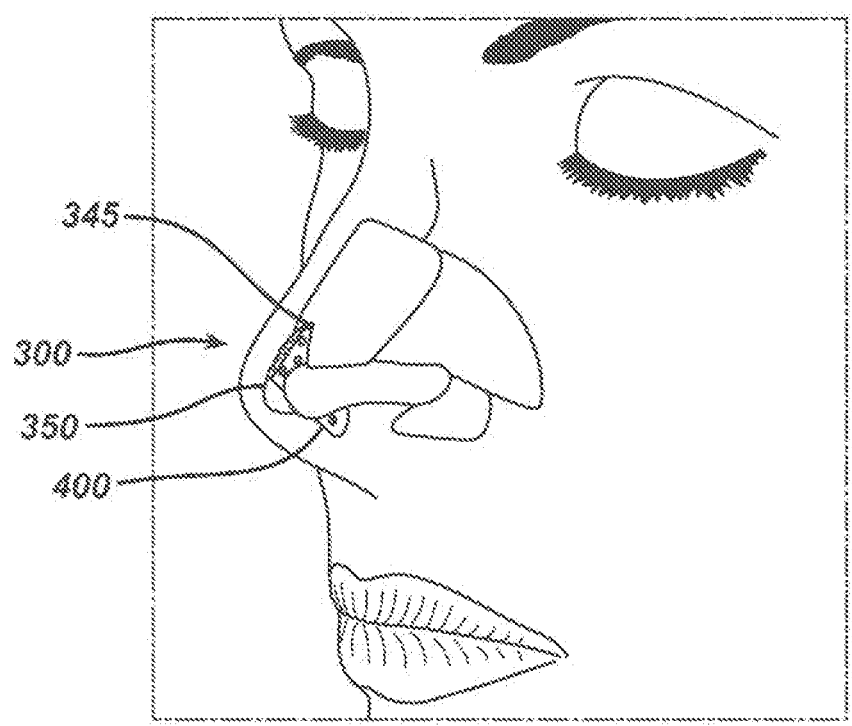
FIG. 15 illustrates the septal extension graft implanted in the patient's nose.
Figure 16:
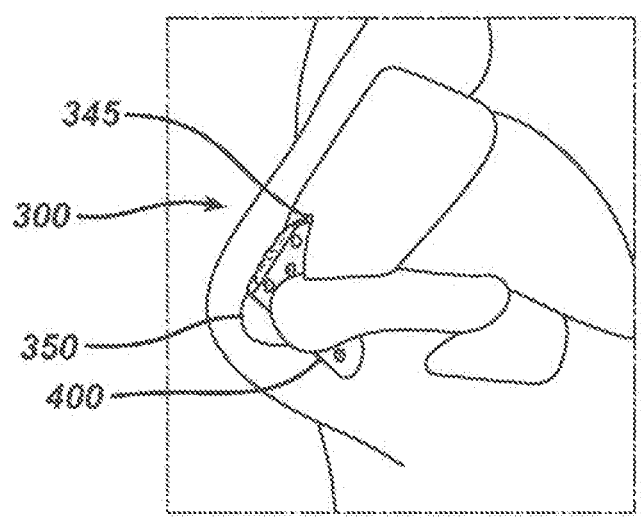
FIG. 16 is an enlarged partial view of FIG. 15.

A patient has insufficient nasal length or an over-rotated nose from previous surgery, which results in significant cosmetic implications. The condition requires surgical intervention and repair. The patient is prepared for nasal reconstructive surgery in a conventional manner including the steps of injecting a local anesthetic, making marginal and/or columellar incisions, elevation of the soft tissue skin envelope and developing appropriate dissection planes. A septal extension graft 400 as seen in FIG. 13A is cut from a universal kit of the present invention as seen in FIG 12 (and trimmed as required) and prepared by securing one or more cartilage fragments to one or both of the side walls using conventional surgical sutures. The septal extension graft is placed caudally and adjacent to the native septum on one or both sides. The wall members of septal extension graft extend over the native septum; the cartilage pieces attached to the septal extension graft are placed as close as possible to the native septum to provide greater stability of the graft. One or both wall members may be trimmed as desired by the surgeon to minimize the foreign body material load; e.g., trimming part of the wall member to leave only supporting strips or struts instead of leaving a complete wall member. The procedure is continued by placing appropriate grafts and using suture techniques to achieve the desired functional and aesthetic results depending on the preoperative assessment and surgical plan. When no other grafts or structure modifications are required the procedure is completed by redraping the soft tissue over the nasal structure and closing the marginal and columellar incision.

The novel bioabsorbable nasal implant devices formed or cut from the bioabsorbable universal kit devices of the present invention have many advantages when used in rhinoplasty and nasal surgical procedures. The advantages include, but are not limited to, shorter operating time with an off-the-shelf product; better predictability of the outcome with desirable and consistent width of the implants; elimination or significant minimization of the need for autografts and allografts; lower risk of long term complications due to complete absorption after the mechanical support is no longer required of the implanted graft; and, improved short and long term cosmetic outcome and patient satisfaction. In addition, the likelihood of revision surgery is decreased with the novel bioabsorbable implants made from the novel bioabsorbable kit devices of the present invention. The advantages also include minimal or no need to harvest cartilage to construct grafts such as a columellar strut graft, which results in shorter procedure and reduced donor site morbidity. The use of the devices results in more predictable long-term outcomes with lower risk of complications.

The universal kit devices of the present invention provide for a novel universal kit made from bioabsorbable polymers that can be used by the health care provider in the field to construct a variety of nasal implants useful in nasal reconstructive surgical procedures that can be customized to each individual patient. The kit devices eliminate the need to have a large inventory of nasal implant devices of varying types and sizes on hand, and provide the surgeon with improved versatility to improve surgical outcomes, and provide the patient with a likely superior aesthetic and functional outcome resulting in improved patient satisfaction.

Although this invention has been shown and described with respect to detailed embodiments thereof, it will be understood by those skilled in the art that various changes in form and detail thereof may be made without departing from the spirit and scope of the claimed invention.

We claim:

1. A biocompatible, bioabsorbable polymeric nasal kit device, comprising: a first wall member having an inner surface, an outer surface, a free top side, a bottom side, opposed lateral ends, and a first height;
    a second wall member having in inner surface, an outer surface, a free top side, a bottom side, opposed lateral sides and a second height, wherein the first height is greater than the second height;
    a spine member having a pre-formed curved cross-section having a concave three dimensional shape, an inner surface and an outer surface, wherein the bottom ends of the first and second wall members are connected to the spine member such that there is a channel defined by the inner surfaces of the first wall member, the second wall member and the spine member;
    wherein the kit device includes a first and a second outline of a nasal implant on at least one surface, the first outline being the shape of a first nasal implant, and the second outline being the shape of a second nasal implant;
    wherein the kit device comprises a bioabsorbable polymer.

2. The kit device of claim 1, additionally containing a plurality of openings through one or more of the wall members.

3. The kit device of claim 1, wherein at least one outline comprises a printed image.

4. The kit device of claim 1, wherein at least one outline comprises a score line.

5. The kit device of claim 1, wherein at least one outline comprises a thermally formed line.

6. The kit device of claim 1, wherein at least one outline is laser cut into the device.

7. The kit device of claim 1, wherein at least one outline is mechanically cut into the device.

8. The kit device of claim 1, wherein at least one outline defines a nasal implant selected from the group consisting of spreader graft members, plates, columellar struts, septal extension grafts, and combinations thereof.

9. The kit device of claim 1, wherein at least one outline defines a plate member.

10. The kit device of claim 1, wherein at least one outline defines a spreader graft member device.

11. The kit device of claim 1, wherein at least one outline defines a columellar strut.

12. The kit device of claim 1, wherein at least one outline defines a septal extension graft device.

13. The kit device of claim 1, wherein at least one of the first and second wall members can partially rotate inwardly or outwardly with respect to the spine member.

14. The kit device of claim 1, wherein the bioabsorbable polymer is selected from the group consisting of polydioxanone, polyglycolide lactide-rich copolymers, and blends thereof.

15. The kit device of claim 1, wherein the bottom sides of the wall members are connected to the spine member by a process selected from the group consisting of welding, gluing, and mechanical fixation.

* * * * *